United States Patent
Stewart et al.

(10) Patent No.: US 7,204,335 B2
(45) Date of Patent: Apr. 17, 2007

(54) VEHICLE SOBRIETY INTERLOCK DEVICE

(75) Inventors: Jeffrey Stewart, Melbourne, FL (US); James McClelland, Cocoa, FL (US); Charles E. Smith, Melbourne, FL (US)

(73) Assignee: Sheram Enterprises, Inc., Marietta, GA (US)

( * ) Notice: Subject to any disclaimer, the term of this patent is extended or adjusted under 35 U.S.C. 154(b) by 460 days.

(21) Appl. No.: 10/485,041

(22) PCT Filed: Oct. 31, 2003

(86) PCT No.: PCT/US03/34650

§ 371 (c)(1),
(2), (4) Date: Jan. 23, 2004

(87) PCT Pub. No.: WO2005/051700

PCT Pub. Date: Jun. 9, 2005

(65) Prior Publication Data

US 2005/0241871 A1 Nov. 3, 2005

(51) Int. Cl.
*B60K 28/00* (2006.01)
(52) U.S. Cl. .................... 180/272; 73/23.3; 307/10.1; 340/576
(58) Field of Classification Search .............. 180/272; 600/532, 558, 405; 340/576; 73/23.3; 436/170; 370/10.1
See application file for complete search history.

(56) References Cited

U.S. PATENT DOCUMENTS

| | | | |
|---|---|---|---|
| 3,764,270 A | | 10/1973 | Collier et al. |
| 3,824,538 A | | 7/1974 | Slemp |
| 3,831,707 A | | 8/1974 | Takeuchi |
| 4,093,945 A | * | 6/1978 | Collier et al. ............... 180/272 |
| 4,592,443 A | * | 6/1986 | Simon ........................ 180/272 |
| 4,697,666 A | | 10/1987 | Collier et al. |
| 4,749,553 A | * | 6/1988 | Lopez et al. .................. 422/84 |
| 4,809,810 A | * | 3/1989 | Elfman et al. .............. 180/272 |
| 4,901,058 A | | 2/1990 | Comeau et al. |
| 4,902,628 A | | 2/1990 | Blair |
| 4,912,458 A | | 3/1990 | Comeau et al. |
| 4,926,164 A | | 5/1990 | Porter et al. |
| 5,291,898 A | * | 3/1994 | Wolf .......................... 600/532 |

(Continued)

*Primary Examiner*—Paul N. Dickson
*Assistant Examiner*—George D Spisich
(74) *Attorney, Agent, or Firm*—Larson +Larson, PA; James E. Larson; Herbert W. Larson

(57) ABSTRACT

An interlock device for measuring the sobriety of a potential vehicle operator is coupled to the starting mechanism of the vehicle. The interlock device includes a microprocessor controlled handset and base unit. The base unit encloses relays to preclude the starting mechanism from engaging if a predetermined acceptable threshold level of blood alcohol content has been exceeded. The relays receive a signal, through the base unit microprocessor, from the handset microprocessor which has calculated the blood alcohol content of a breath sample introduced into the handset by the vehicle operator. A breath sampling housing is enclosed within the handset in axial alignment with an intake port of the handset. A water filter and valve are positioned upstream from an electrochemical fuel cell. The fuel cell is coupled to the microprocessor. A pressure transducer measures the pressure of the breath sample. The handset microprocessor calculates a pressure offset through an algorithmic equation and applies the offset to the variable reading across the fuel cell to provide a normalized blood alcohol content measurement.

38 Claims, 14 Drawing Sheets

U.S. PATENT DOCUMENTS

| | | | |
|---|---|---|---|
| 5,426,415 A * | 6/1995 | Prachar et al. | 340/576 |
| 5,805,079 A | 9/1998 | Lemelson | |
| 6,026,674 A * | 2/2000 | Gammenthaler | 73/19.01 |
| 6,075,444 A | 6/2000 | Sohege et al. | |
| 6,167,746 B1 | 1/2001 | Gammenthaler | |
| 6,234,006 B1 * | 5/2001 | Sunshine et al. | 73/29.01 |
| 6,512,465 B2 | 1/2003 | Flick | |
| 6,609,068 B2 | 8/2003 | Cranley et al. | |
| 6,792,793 B2 * | 9/2004 | Mendoza | 73/23.3 |
| 6,853,956 B2 * | 2/2005 | Ballard et al. | 702/183 |
| 6,967,581 B2 * | 11/2005 | Karsten | 340/576 |
| 2002/0084130 A1 | 7/2002 | Der Ghazarian et al. | |
| 2003/0176803 A1 | 9/2003 | Gollar | |
| 2003/0183437 A1 * | 10/2003 | Mendoza | 180/272 |
| 2004/0239510 A1 * | 12/2004 | Karsten | 340/576 |

* cited by examiner

VEHICLE SOBRIETY INTERLOCK DEVICE

PRIOR APPLICATION

This application bases priority on International Application No. PCT/US03/34650, filed Oct. 31, 2003.

BACKGROUND OF THE INVENTION

1. Field of the Invention

This invention relates to an improved sobriety interlock device. More particularly, it relates to a sobriety interlock device for use in vehicles and motorized machinery apparatus, the device incorporating anti-circumvention features and an improved sampling system to provide for more accurate measurements of the blood alcohol content of an unsupervised operator of a vehicle or motorized machinery apparatus.

2. Background of the Prior Art

Breathalyzer testing and sobriety interlock devices for use in vehicles (automobiles) and motorized machinery for industry are well known in the prior art. These types of devices work on a principle that the breath of a person who has consumed alcoholic beverages can be sampled to determine a corresponding blood alcohol content (blood to alcohol ratio) of that person. Using known levels of blood alcohol content, it can then be determined whether someone has too much alcohol in their system which would effect their ability to operate machinery or a vehicle. For instance, many states use a level of 0.08 as a percentage of blood alcohol content which acts as a presumption that a person is intoxicated and unable to drive a vehicle.

Early advancements in breathalyzer testing devices can be seen in U.S. Pat. No. 3,764,270 to Collier et al. wherein an alcohol concentration measuring apparatus is disclosed. In this reference it is noted that the operation of vehicles and machinery by persons intoxicated by alcohol is a major health problem in many places in the world and especially in the United States. The device of this prior art reference teaches that deep lung breaths are required to measure an accurate blood alcohol content from a gas sample or more accurately, the breath. Accordingly, improvements over then existing prior art devices are made in this Collier et al. reference that address measuring the alcohol concentration by ensuring a continuous and uninterrupted flow of gas from a subject using such device. However, it is not contemplated that this device could then be interfaced with the starting mechanism of a vehicle in the event that a predetermined threshold of the measured blood alcohol content is exceeded. This feature is clearly needed.

Subsequent devices seen in the prior art have addressed the need for a sobriety measuring device to be interfaced with a vehicle's starting mechanism—a so called "interlock" device. For instance, U.S. Pat. No. 3,831,707 to Takeuchi describes an early interlock device which takes a series of measurements to determine the temperature, humidity and alcohol concentration of the vehicle operator's breath. These measurements can be taken after the ignition switch of the vehicle (i.e., automobile) is engaged, thereby permitting the operator of the vehicle to warm up the car, by blowing into a sampling apparatus. Predetermined permitted ranges are set within the device for these three measurements. If the three readings fall within the permitted ranges (all three conditions pass), the automobile's transmission can be engaged and the car can be operated. If not (the test fails), the transmission of the automobile will not engage thereby preventing operation of the vehicle based upon an assumption that the operator is intoxicated and therefore lacking the required mental faculties to operate the vehicle. The temperature and humidity readings are used to sense that the air subjected to the sampling apparatus is in fact a human breath. Accordingly, these readings assist somewhat in the anti-circumvention of the interlock device. However, temperature and humidity can fluctuate substantially depending on the climate in which the vehicle is located and thereby effect the test being taken. Accordingly, there is a great need to improve upon temperature and humidity sensing systems that work in coincidence with the alcohol sensors to provide more accurate measurements for interlock devices. Further, other more sophisticated anti-circumvention features are needed in interlock devices to thwart attempts by users to fool the device thereby permitting their vehicle to be operated when it clearly should not.

Other advancements in the prior art for sobriety interlock devices have been made that do not directly address temperature and humidity sensing. In particular, advancements in measuring a continuous and uninterrupted flow of breath for the sampling device can be seen in U.S. Pat. No. 4,093,945 to Collier at al. which again addresses the need for sampling a deep lung breath since it is known that, absent some flow rate measurement equalization algorithm within an interfacing software program, deep lung breath samples are more apt to provide an accurate measurement of the blood alcohol content of the test taker than a short and shallow breath. The device of this prior art reference works to exclude breath samples that are not deep lung samples thereby requiring the individual taking the test to repeat the test until the device indicates that the breath sample was a deep lung breath sample. Unfortunately, this device can be difficult to use since not all individuals are capable of providing a deep lung sample needed to take the measurement. Improvements for measuring the flow rate of the breath samples are certainly needed. Such improvements should utilize an interfacing software program that can operate to equalize the breath samples through algorithmic offset calculations regardless of how deep or how shallow they are to provide the most accurate measurement possible.

Still other advancements in prior art interlock devices address operator identity. Since most states in the U.S. have already mandated the use of interlock devices for convicted DUI (driving under the influence of alcohol) offenders, operator identity of an unsupervised test can be critical. It is quite reasonable to assume that an inebriated vehicle operator may simply ask a sober person to take the test for them so that the vehicle starting mechanism can be engaged upon receiving a "pass" result since the test would be otherwise unsupervised. Although this act in itself is probably punishable by a fine or even incarceration in most states, it most likely has occurred and will continue to occur in the future. Accordingly, the inventions seen in U.S. Pat. No. 4,738,333 to Collier et al. and U.S. Pat. No. 4,809,810 to Elfman et al. and U.S. Published Application No. U.S. 2002/0084130 to Der Ghazarian et al. were developed to address operator identity so that the person mandated (by a Court for example) to take the sobriety test before the vehicle can be operated is the individual actually taking the test. It is important to note however, that these interlock devices are known to be more complicated and thereby require more maintenance/calibration, more expense and more sophisticated circuitry. Although there is a great need to ensure that the proper person is taking the sobriety test, such complicated and expensive devices may be overlooked and not employed due to their over-sophistication. There is clearly a need to keep sobriety interlock devices simple in their design but accurate in their measurement. Other, more simpler anti-circumvention technology should be used to ensure that drunk drivers are kept off the road. Development of a secure anti-circumvention interlock device that does not involve complex personal identity scans is clearly needed.

Most modern interlock devices include a few common elements: a power supply, a fuel cell (alcohol sensor), a sampling system (a breath intake channel leading to the fuel cell), a microprocessor to analyze the results of the test taken by the fuel cell and an output (a relay connected in series with the starter of the vehicle). In breath analyzer devices (those which are not used as interlock devices), output relays are not necessary since such devices are not intended to prevent the operation of a vehicle but merely used to give a blood alcohol content measurement. However, other common elements can be found, even though their uses may vary. Indicative of the use of a microprocessor in a breath analyzer device (but not that necessarily of an interlock device), as shown in U.S. Pat. No. 4,749,553 to Lopez et al., a microprocessor is employed to calculate the blood alcohol content by running an algorithm contained within the memory of the microprocessor using a plurality of signals-generated by taking a sample breath, including: an alcohol signal, a distance signal to compensate for diffusion of the exhaled breath, a pressure signal and a temperature signal. These types of signals are known as environmental signals and are helpful in securing a more accurate blood alcohol content measurement based upon ambient environmental conditions which may effect the measurement and give a false positive (a test fail). However, this device lacks important anti-circumvention features which are needed for use in interlock devices for preventing false measurements intended to "fool" the analyzing device. Anti-circumvention features are critically needed in interlocking devices since almost all measurements are taken in an unsupervised location. Further, the actions of DUI offenders under a court order to have the interlocking devices installed in their automobile will be under review. It will be imperative for the supervising agency (i.e., Probation Officer) to determine whether the interlocking devices have been circumvented, tampered with or not used when instructed (i.e., "rolling repeat tests"). Accordingly, use of data logs should be employed as a deterrent to the person mandated to use the device as well as for use in monitoring the life and proper function of the interlocking device.

One example of device circumvention includes using a gas source other than a current human breath, say from a balloon, to fool the device into thinking that an actual test is being made. One method to prevent such circumvention can be seen in the device of U.S. Pat. No. 4,902,628 to Blair. This device requires a positive and negative breath sample (blowing then sucking) to provide a measurement of the breath being tested and hence the blood alcohol content of such person. This device is first blown into by the person being tested, then the person is required to apply a suction after a short time lapse. Accordingly, a first and second signal are generated. If both signals are not recognized by a control means, a measurement will not be provided, the test will fail and the vehicle will not be permitted to start. This helps to ensure that an improper gas is not used to take a test on a device that merely requires the person to blow into such device. However, this type of device still could improved by employing enhanced anti-circumvention features.

In order that an accurate reading of the blood alcohol content is measured, it is important that the fuel cell not be exposed to too much pressure from a strong breath sample or too little pressure from a shallow or weak breath sample. Some prior art devices have attempted to address this problem. In those devices that utilize a valve upstream from the fuel cell, some have used a pressure transducer to control the opening and closing of the valve. This can be seen in U.S. Published Application No. U.S. 2003/0176803 to Gollar. In such device, the pressure transducer measures the pressure of the gas sample (human breath) and controls the opening of the valve in response to the measured pressure—a so called "constant volume" sampling system. This device integrates a pressure feedback signal to obtain a volumeric equivalent. The valve time opening varies from sample to sample based upon the measured pressure. In other words, the opening of the valve is directly dependent on the measurement taken by the pressure transducer.

A similar prior art device can be seen in U.S. Pat. No. 6,167,746 to Gammenthaler which utilizes a normally closed valve. The valve opens to control the volume of the breath sample by measuring the pressure of the breath flow through the device and, in response to the measured pressure, electronically controls the opening of the valve and diverts a portion of the breath flow into the fuel cell. A valve controller limits the duration of time that the valve is open based upon the measured pressure of the breath flow. In other words, the valve is dependent on the valve controller which in turn is dependent on the pressure measuring device.

An improved device is clearly needed wherein the valve works independently of the pressure transducer and permits a breath sample to pass there through without regard to the amount of pressure in the sample. The improved device should instead compensate for varying pressures through an algorithmic calculation and not through electronic valve controllers and pressure measuring devices.

It is clearly seen that an improved interlock device is needed which can provide for a more accurate blood alcohol content measurement all the while having the necessary anti-circumvention features that ensures individuals will use the device as intended. The device should be less complicated then those devices seen in the prior art such that greater ease of operation can still be achieved. Improved accuracy should be enjoyed through a microprocessor controlled valve working independently from a pressure sensitive component. The improved device should permit the logging of data relative to the operation of the device so that a supervising agency can review the log to see if circumvention or tampering of the device has occurred and to otherwise see that the device is working properly. Other features that monitor the status of the vehicle's movement would also help to ensure that circumvention is not attempted through idling of the vehicle while the person consumes alcohol away from the car that has already been started. Further, rolling repeat tests during operation of the automobile would help to ensure that alcohol is not being consumed by the driver during operation of the vehicle after it has been started (i.e., driving down the highway and consuming alcohol). Other improvements are also needed to ensure that the most accurate measurement is always provided. For instance, through the use of water filtering, moisture can be virtually eliminated from the breath vapor thereby avoiding moisture saturation of the fuel cell (the alcohol sensor). Improvements in temperature monitoring and temperature control of the device should also be practiced to ensure that the device works properly in cold weather climates.

SUMMARY OF THE INVENTION

We have invented an improved vehicle sobriety interlocking device that overcomes all of the short comings seen in the prior art. Our device utilizes a base unit and handset in communication with one another and which are installed within close proximity of the driver's seat of a vehicle or motorized machinery. The base unit includes at least one relay which is electrically wired in series with the starter of the vehicle. The handset is microprocessor controlled and is used as the breath testing device and analyzer. Both the base unit and handset can be powered from the 12V DC battery of the vehicle. The base unit also contains a microprocessor which interfaces with the handset microprocessor through a high speed serial data interface.

Our device includes a handset having a front and back portion enclosing a printed circuit board. Included on the printed circuit board is a microprocessor which interprets a breath sample taken from a sampling system within the handset and thereafter sends a high speed serial data signal to the base unit microprocessor for controlling a set of relays. If the result of the sobriety test is that a predetermined threshold (for example 0.03%) has not been exceeded, then the appropriate signal is sent so that the relays change state thereby permitting the starter of the vehicle to be engaged and the vehicle to be operated. If the result of the test is that the predetermined threshold has been exceeded, then an appropriate signal is sent such that the relays do not change state whereby the starter can not be engaged and hence the vehicle can not be operated (precludes ignition). An LED display coupled to the microprocessor instructs the user when to blow and whether the test taker passed or failed the sobriety test. Other messages can be displayed, including, but not limited to, the number of days remaining before the next servicing, before the next monitoring (i.e., download) or before the next calibration.

Enclosed within the handset is a sampling system housing in communication with a breath intake port forming a breath channel. The sampling system housing includes a body portion, a fuel cell, a solenoid valve, a water filter, a housing heater, a temperature sensor and a capillary tube attached at a first end to the water filter and at a second end to a pressure transducer mounted on the printed circuit board. The breath channel has a temperature sensor mounted through the housing body for determining whether the gas sample is that of a current human breath. The water filter reduces the amount of moisture that is exposed to the fuel cell by passing alcohol vapors while precluding water in the gas sample from reaching the fuel cell. The solenoid valve is positioned upstream from the fuel cell and remains open for a finite period of time to pass the gas sample to the fuel cell. The handset microprocessor controls the opening and closing of the solenoid valve. The solenoid valve is open for a constant and finite, albeit short, period of time. The pressure transducer is coupled to the microprocessor but does not control the opening and closing of the solenoid valve but instead works to normalize the breath samples that are introduced to the breath channel through an algorithmic calculation.

A proprietary software program embedded upon the microprocessor interprets the pressure levels of the breath samples and equalizes the measurements made across the fuel cell by calculating an offset through the mathematical algorithm based upon predetermined standard breath samples. Accordingly, a standard alcohol response equation is programmed in the microprocessor. During calibration of the interlock device, the handset determines appropriate valve opening time required to achieve a particular sample based upon predetermined pressure (an example of a particular sample is 0.03% blood alcohol content). Once this value is determined, the valve opening time is fixed for each interlock device until the next time the handset is calibrated.

The pressure measurements that are used to normalize the breath samples are taken by the pressure transducer at some finite time after the solenoid valve first receives flow through the valve. The calculated offset ensures that higher flow rates due to higher pressure readings do not give false positive readings (the reverse also being true; ensures that lower flow rates due to lower pressure readings do not give off false negative readings). These components provide a more accurate reading for the novel interlock device of the present invention and also work as an anti-circumvention feature whereby the user can not fool the device by introducing a shallow low pressure breath sample.

A pair of accelerometers are mounted on the circuit board of the base unit to constantly measure movement of the vehicle in either an X or Y axis. These measurements are used to determine whether the vehicle is moving (i.e., accelerating) or turning. Accordingly, the accelerometer can be used as an anti-circumvention feature for the interlock device of the present invention. Results of these measurements are recorded in a data log which can be downloaded by a supervising agency. The data log will show whether the car was idling for any questionable amount of time. This acts as a deterrent against court mandated users from starting their vehicle when they are completely sober, driving to an establishment serving alcoholic beverages, leaving their vehicle running (idling) while they consume alcohol and then return to their vehicle to drive away drunk. Also, the accelerometers act as a bypass detector to determine whether the vehicle was moving at a time when no test by the interlock device was first initiated (vehicle was started without an interlock device test being performed).

Other anti-circumvention features include rolling repeat tests whereby the user has to blow into the mouthpiece of the handset while driving to ensure that alcohol has not been consumed since the vehicle was started. Although the interlock device of the present invention will not disable a running vehicle in the event of a failed test, the data log will record such event and expose the violation to the supervising agency at the time of download of the data log. Further, relays can switch on lights and blow the horn to attract attention to the violator. A mini USB B port is in communication with the handset microprocessor and acts as a point of download for the data log as well as an upload point for supervisor preferences and settings. Downloads and uploads can also be effected through wireless transmission. A second proprietary software program can be used on a laptop or PC to set preferences and settings for the interlock device, to perform calibrations and to interpret the data log.

As used herein, vehicles and motorized machinery apparatus include, but are not limited to, automobiles, trucks, ships motorcycles, boats, planes, trains, tractors, mowers and other industrial and construction vehicles which include a motor and an ignition system.

BRIEF DESCRIPTION OF THE DRAWINGS

The invention can be best understood by those having ordinary skill in the art by reference to the following detailed description when considered in conjunction with the accompanying drawings in which.

DETAILED DESCRIPTION OF THE INVENTION

Figure 1:
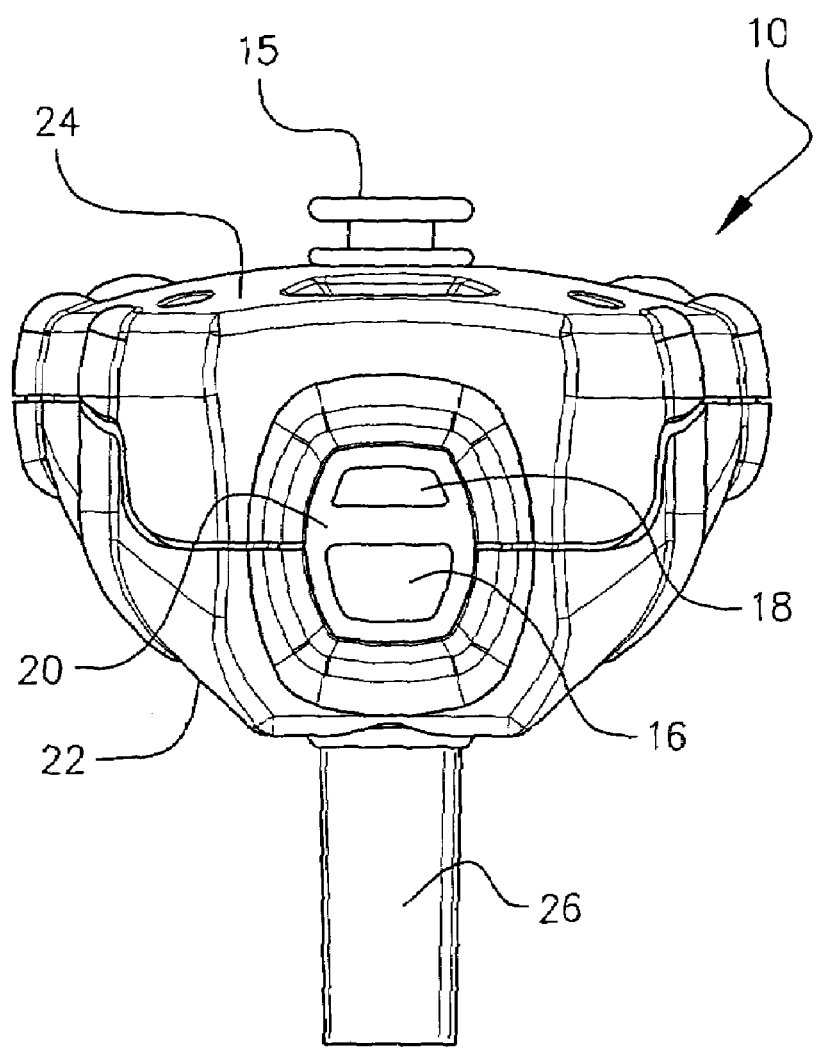
FIG. 1 is a top plan view of a handset used with an interlock device of the present invention.

Throughout the following detailed description, the same reference numerals refer to the same elements in all figures.

Figure 2:
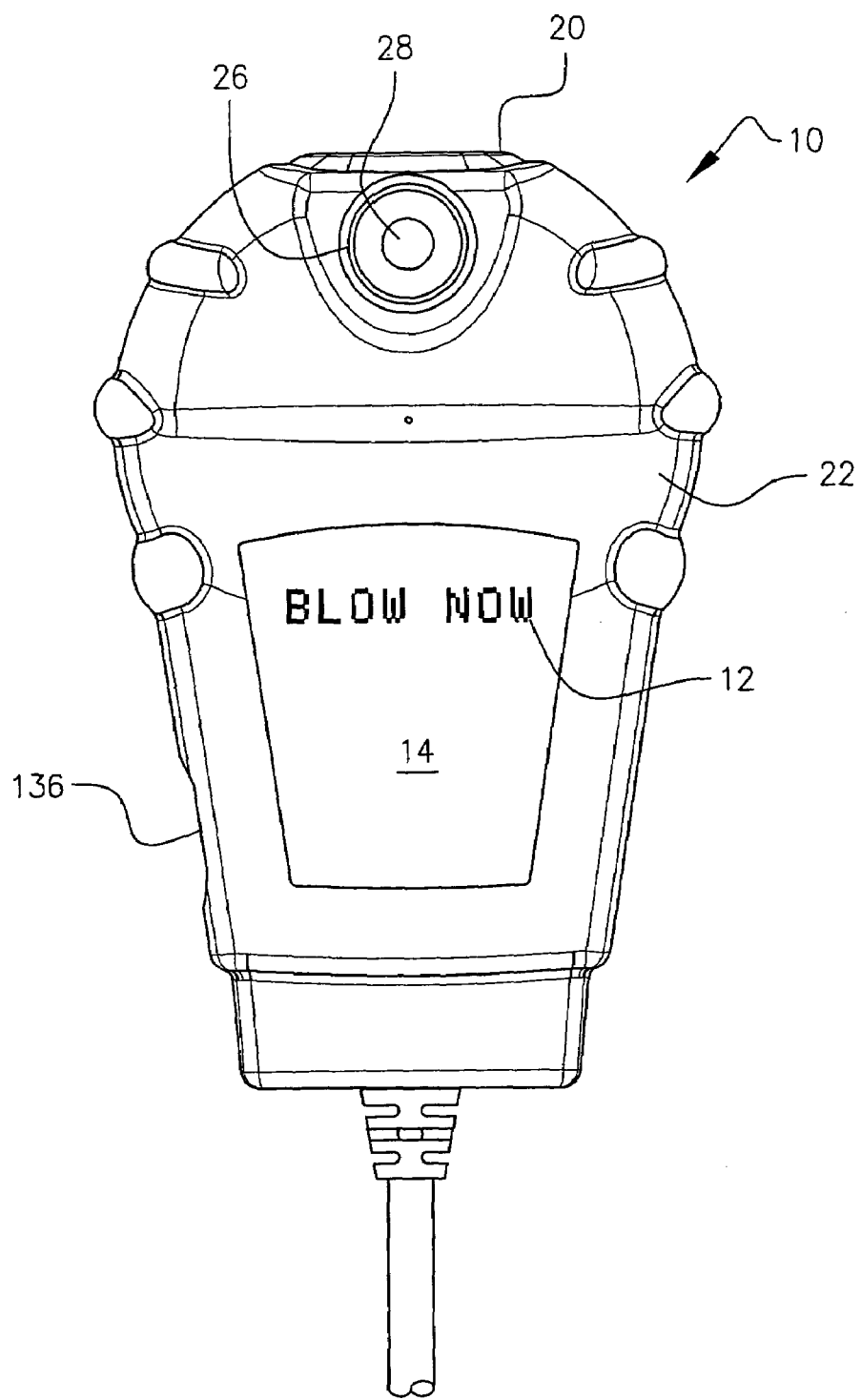
FIG. 2 is a front elevational view of the interlock device handset of the present invention depicting an LED display employed within the device handset.

Referring to FIG. 2, a handset 10 of an interlock device of the present invention is shown. FIG. 2 illustrates a front view of handset 10 whereby a display screen 12 is clearly seen. Display screen 12 is an LED display screen (see FIG. 5) coupled to a printed circuit board (to be discussed hereinafter) enclosed within handset 10 which provides for a plurality of messages to be displayed thereon, including, but not limited to, "Warm Up", "Blow Now", "Fail" and "Pass". LED display screen 12 is covered by a tinted translucent cover 14 so that the messages on display screen 12 are visible but all other components mounted on the circuit board are not visible. As shown in FIG. 2, handset 10 has a conical shape thereby permitting handset 10 to be easily gripped by a person utilizing the interlock device.

Referring now to FIG. 1, it is shown from a top plan view that handset 10 includes a "power-on" button 16 that is first engaged to operate the interlock device of the present invention. Button 16 is located on a top portion 20 of handset 10. When depressed, button 16 sends a signal to a microprocessor which "wakes-up" handset 10 and the interlock device. The interlock device of the present invention can be programmed to "time out" after a pre-determined amount of time has elapsed thereby eliminating the need for the interlock device to be powered down after each use. The interlock device essentially enters a sleep mode and waits for its next instruction to operate. However, in the alternative, the interlock device can be programmed so that it can be powered down by depressing button 16 again or simply shut off when the power source of the interlock device and handset 10 is shut down (i.e., power to an automobile in which the interlock device of the present invention is connected is shut off). Handset 10 also includes a "power on" indicator LED (not shown) positioned underneath a small cover 18 positioned juxtaposed button 16 on handset top portion 20. The indicator LED will illuminate a color, such as green, to indicate that power is being received by handset 10.

Figure 4:
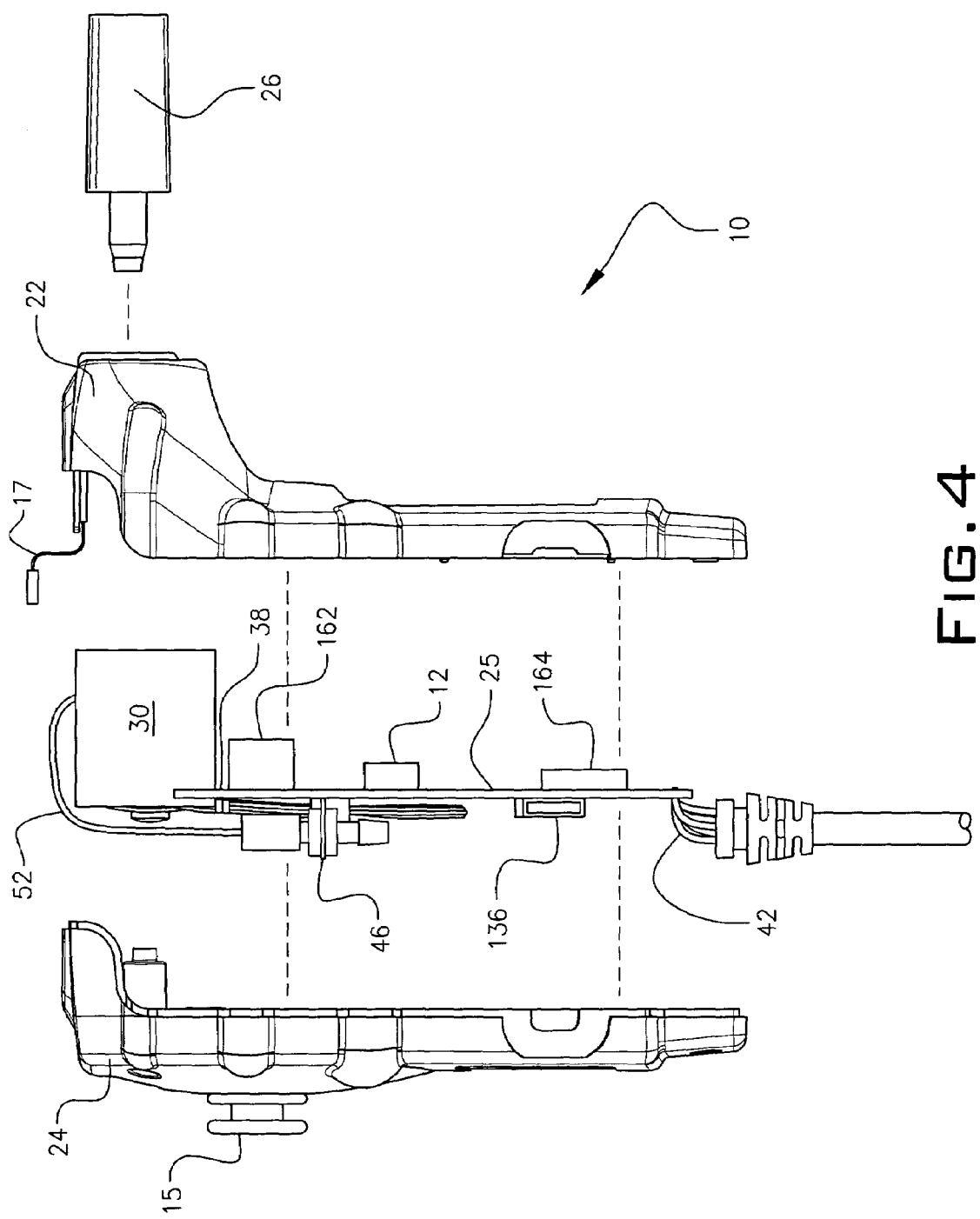
FIG. 4 is an exploded view of the interlock device handset of the present invention.

As shown in FIG. 4, handset 10 includes a front and back housing member, 22 and 24 respectively, which are used to enclose a printed circuit board (PCB) 25 within handset 10. PCB 25 contains various electrical components used for analyzing a breath sample of which will be discussed in further detail hereinafter. The two housing members 22 and 24 are attached by a plurality of screws entering back housing member 24 and inserting into front housing member 22. The "power-on" indicator LED, positioned underneath cover 18, and push button 16, as seen in FIG. 1, communicate with PCB 25 through ribbon connector 17.

With continuing reference to FIG. 4, handset 10 also includes a mouthpiece 26 used to place between the lips of a person utilizing the interlock device of the present invention.

Figure 3:
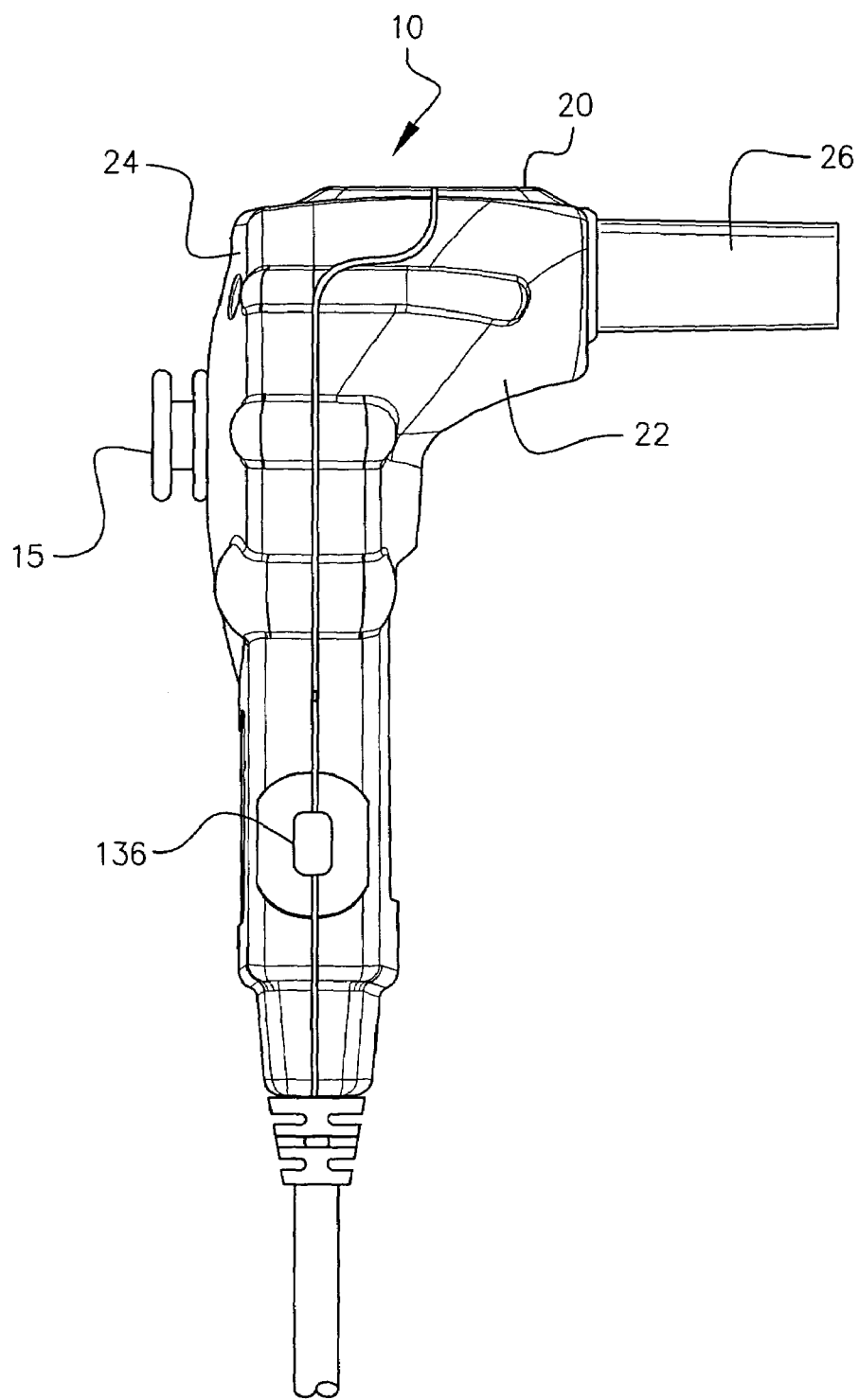
FIG. 3 is a left side elevational view of the interlock device handset of the present invention.
Figure 12:
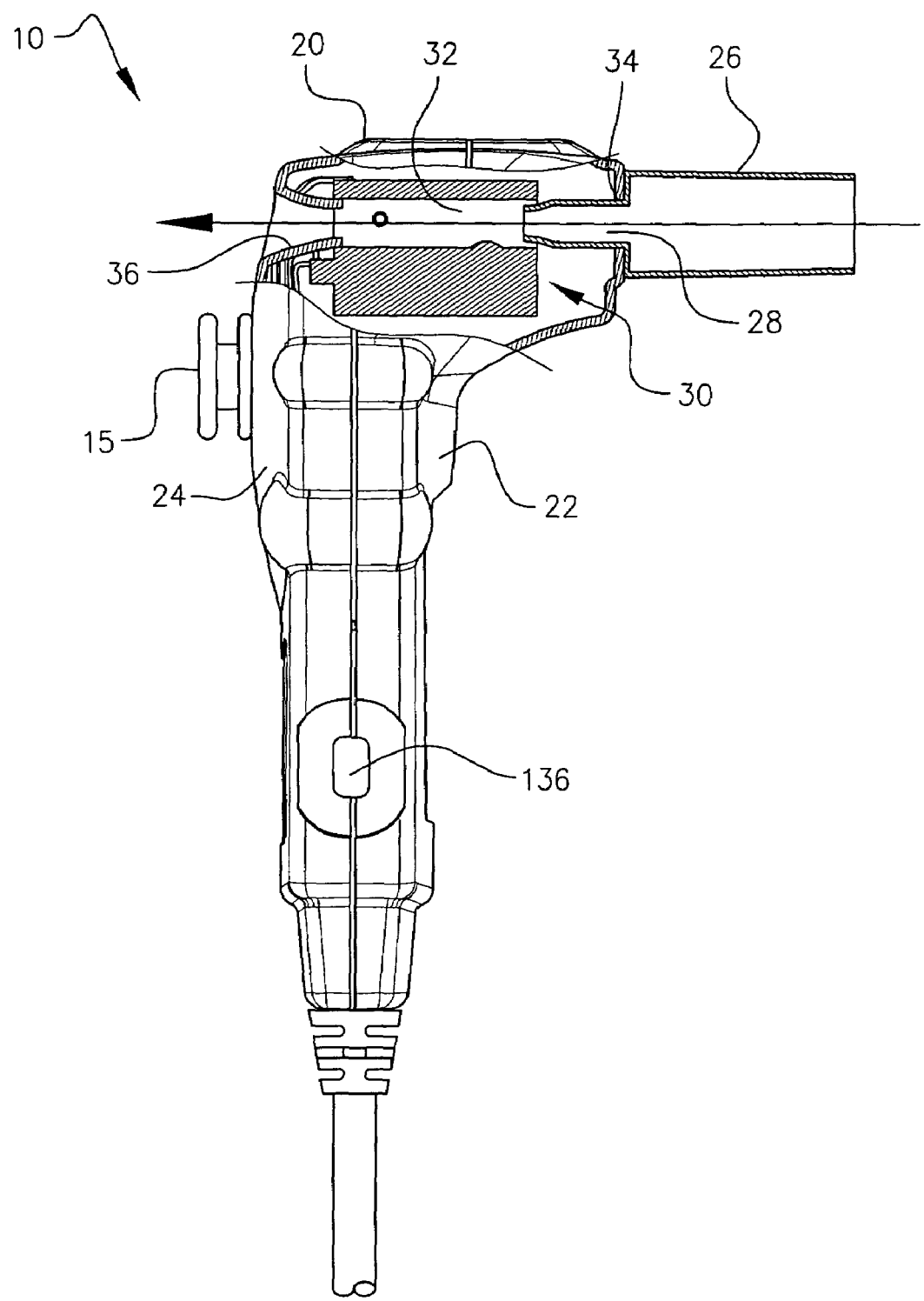
FIG. 12 is a left side elevational view, partially in section, of the interlock device handset of the present invention.

Mouthpiece 26 axially aligns with a breath intake channel 28 which is formed through handset top portion 20 (see FIG. 12). In the preferred embodiment, mouthpiece 26 is secured by friction in handset top portion 20 so that it can be easily removed and replaced when necessary by a small amount of force but is retained if handset 10 is moved around. As shown in FIGS. 1, 3 and 4, a small annular mounting peg 15 is disposed along handset back housing member 24 for hanging handset 10 on a reciprocal clip (not shown) within a vehicle.

Figure 9:
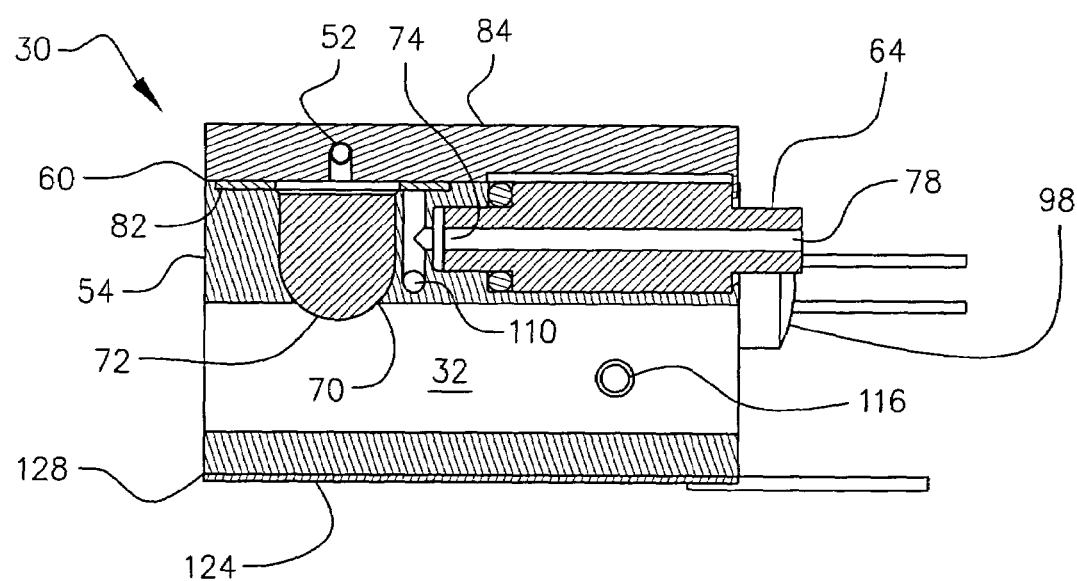
FIG. 9 is a cross-sectional view of the breath sampling housing along lines 9—9 of FIG. 8.
Figure 10:
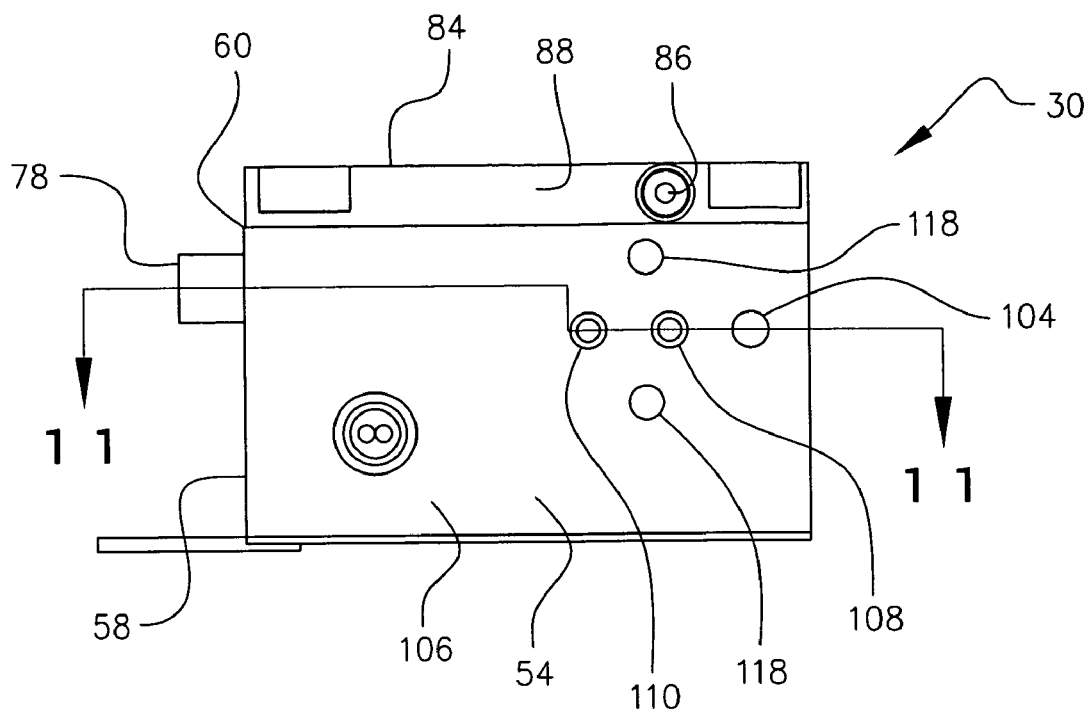
FIG. 10 is a right side elevational view of the breath sampling housing.
Figure 11:
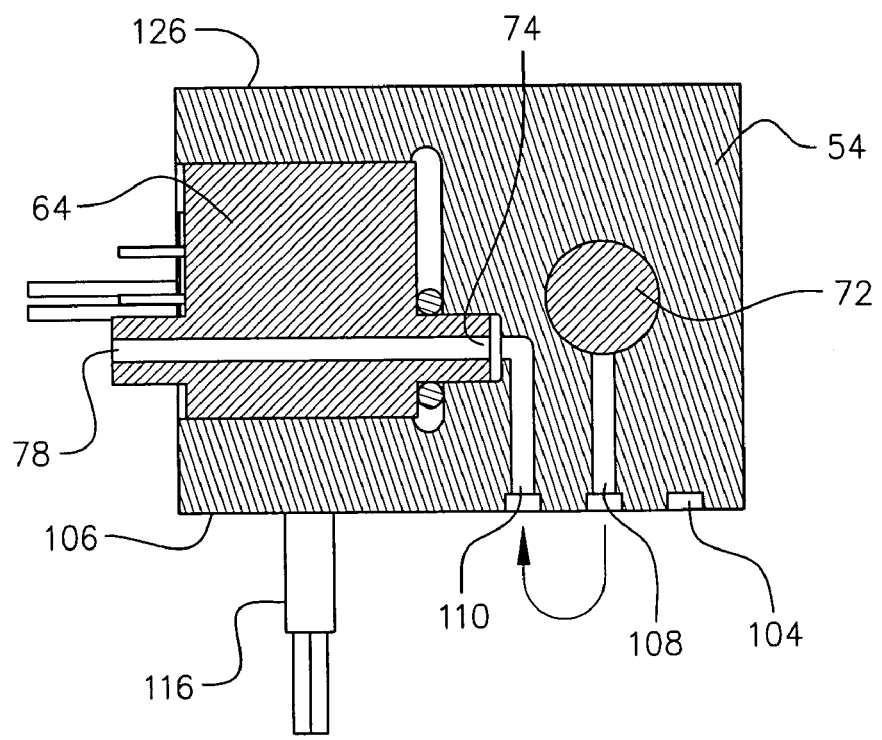
FIG. 11 is a is a cross sectional view of the breath sampling housing along lines 11—11 of FIG. 10.

As shown in both FIGS. 3 and 4, handset top portion 20 projects outwardly. This permits a breath sampling housing 30 to be positioned within handset top portion 20 as illustrated in FIG. 4. Breath sampling housing 30 contains components used to sample the alcohol content of a breath sample blown into mouthpiece 26. Breath sampling housing 30 contains a breath sampling channel 32 (see FIG. 9) which axially aligns with mouthpiece 26 and is positioned intermediate an entrance port 34 and an exhaust port 36 of handset breath intake channel 28 (see FIG. 12).

With continuing reference to FIG. 12, it can be seen how a gas sample enters handset breath intake channel entrance port 34, permits a portion of said gas sample to enter the breath sampling channel 32 of breath sampling housing 30, thereafter expelling all remaining portions of said gas sample out through handset breath intake channel exhaust port 36. For the purposes herein, and for the preferred embodiment of the present invention, gas sample means a human breath possibly containing a level of alcohol vapors within the breath.

Figure 5:
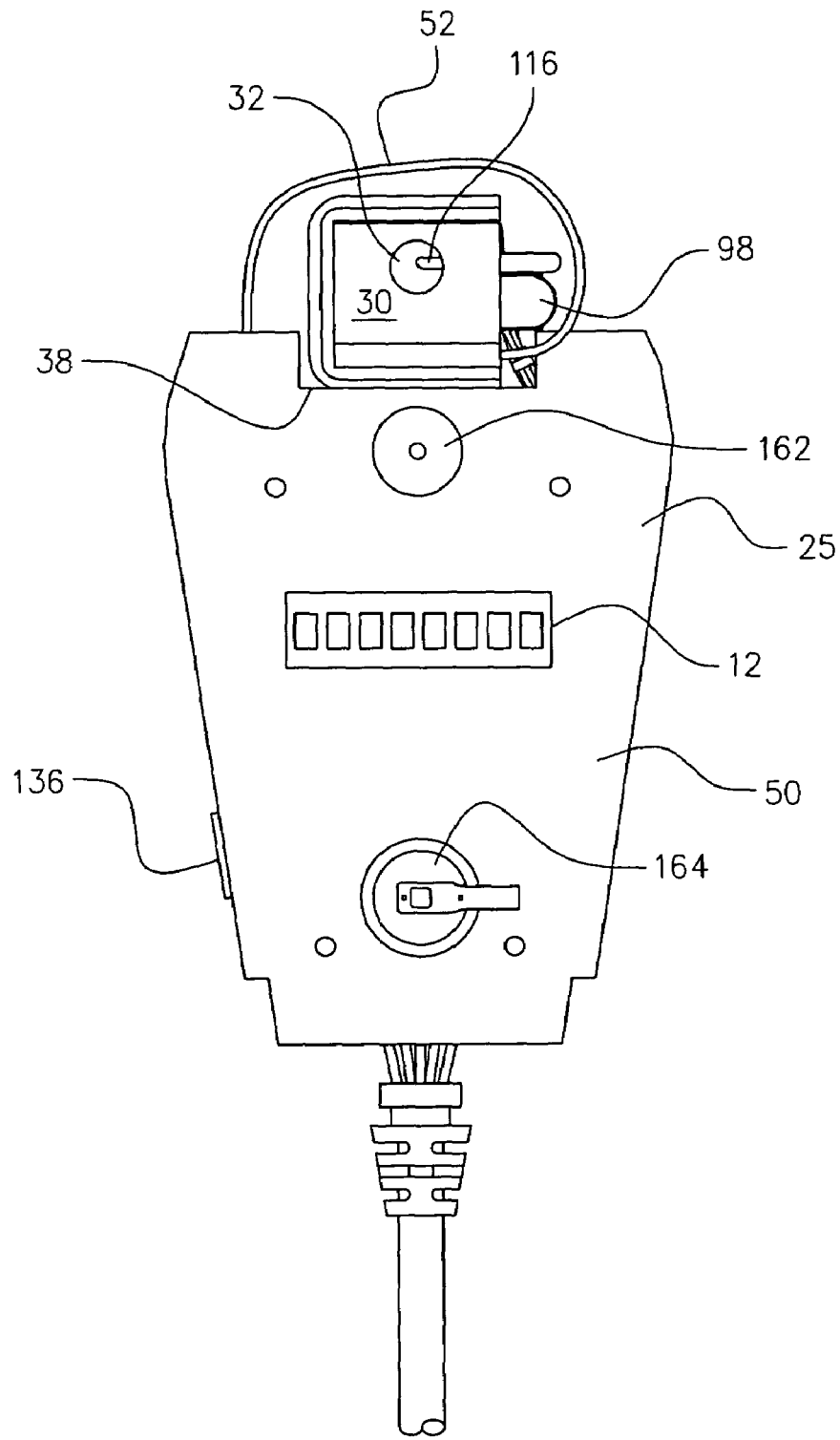
FIG. 5 is a front elevational view of a printed circuit board having a breath sampling housing mounted on a top portion thereof employed within the interlock device handset of the present invention.
Figure 6:
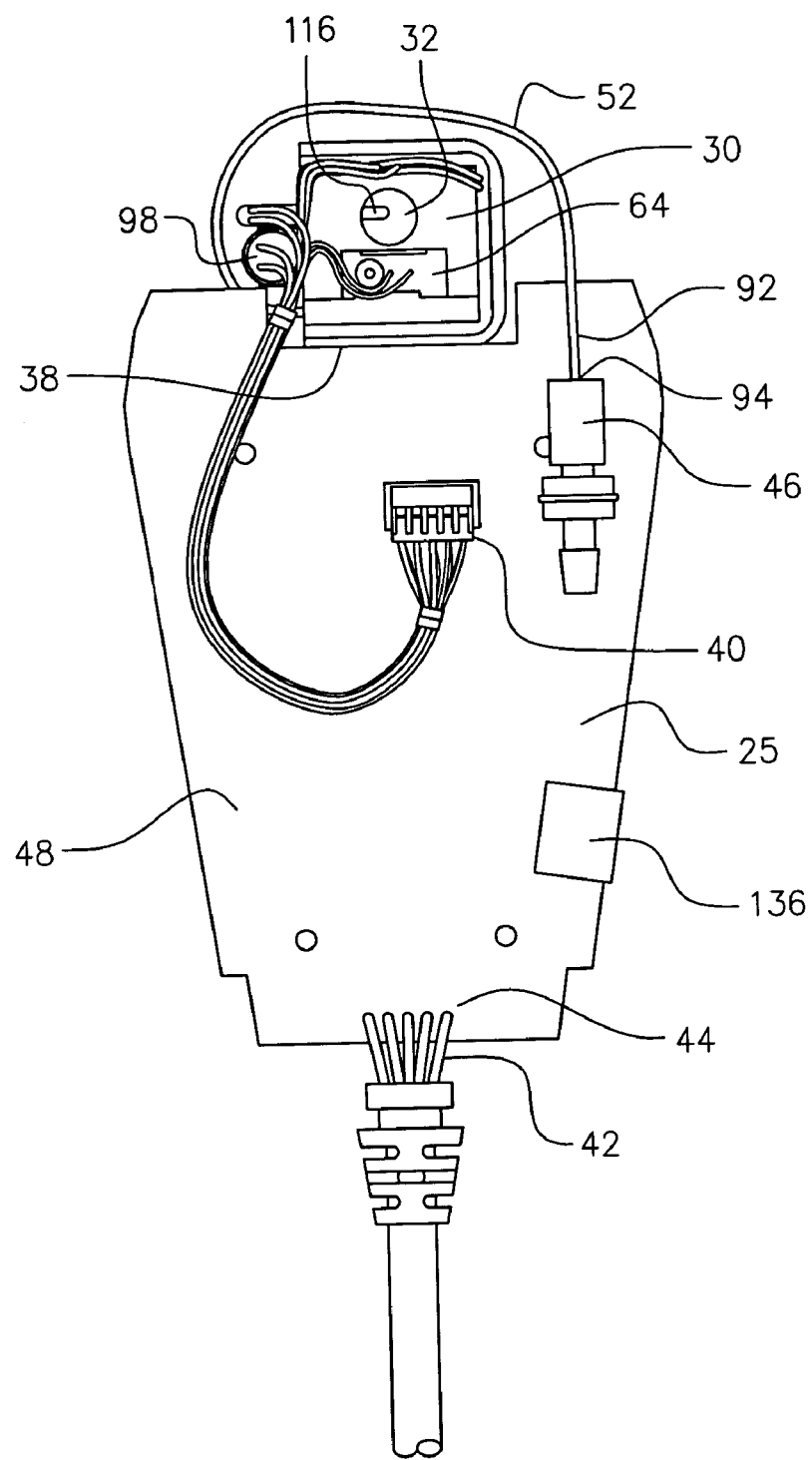
FIG. 6 is a rear elevational view of the printed circuit board having the breath sampling housing mounted on the top portion thereof employed within the interlock device handset of the present invention.
Figure 15:
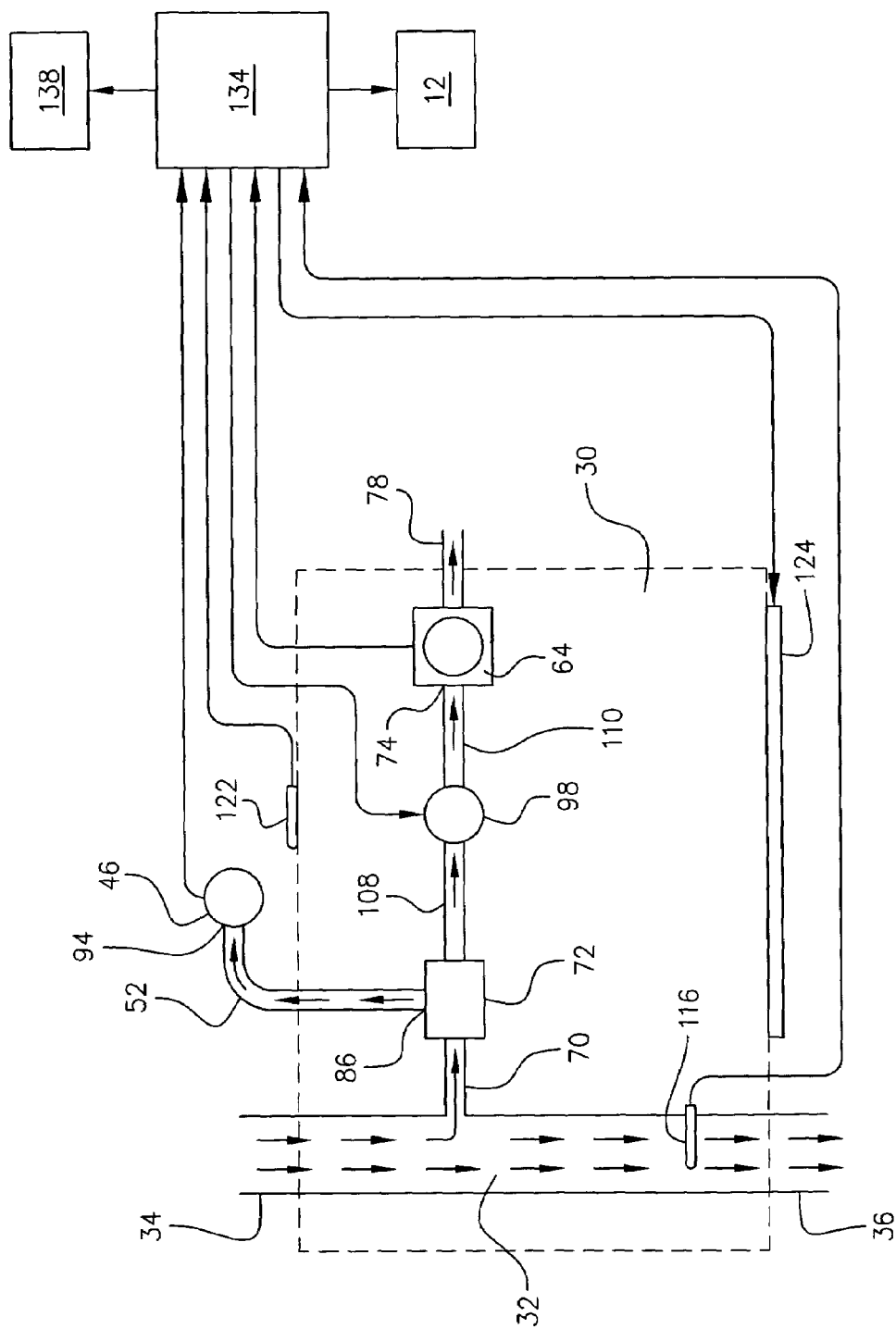
FIG. 15 is a flow diagram illustrating the manner in which air flows through the handset and the breath sampling housing and how certain measuring components of the interlock device of the present invention interact.

As shown in FIG. 6, breath sampling housing 30 mounts on a top portion 38 of PCB 25. Power to all components of breath sampling housing 30 is supplied via a first connector 40 mounted on a back side 48 of PCB 25. In the preferred embodiment, first connector 40 is a removable jumper, although first connector could be a soldered contact. PCB 25 receives its supply of power via a second connector 42 along a bottom portion 44 of PCB 25 which connects to a power source (i.e., battery—not shown) of an automobile or vehicle in which the interlock device is installed. In the preferred embodiment, second connector 42 is a soldered contact, although second connector could be constructed as a removable jumper. PCB 25 also includes a pressure transducer 46 mounted on PCB 25 back side 48. Pressure transducer 46 has a capillary tube 52 connected thereto (see FIG. 6) which feeds to breath sampling housing 30 (see FIG. 5). As shown in FIG. 15, capillary tube 52 directs a small portion of the gas sample entering breath sampling housing to pressure transducer 46 to determine a pressure value of said gas sample. As will be discussed in further detail hereinafter, the measured pressure value of the gas sample is used to calculate an offset, through an algorithmic calculation, which in turn is used to provide compensation such that an accurate measurement of the alcohol content of the gas sample can be provided.

With reference to FIG. 5, PCB 25 also includes a speaker 162 and a battery 164, both coupled to PCB 25 along front side 50. Speaker 162 provides audio signaling for power-up and power-down procedures, an indicator for test results, an indicator for circumvention warnings and as an indicator that a rolling repeat test may be required. Battery 164 supports a microprocessor of handset 10 (to be discussed in further detail hereinafter) and a clock (not shown) for handset 10, both located on PCB 25.

Figure 7:
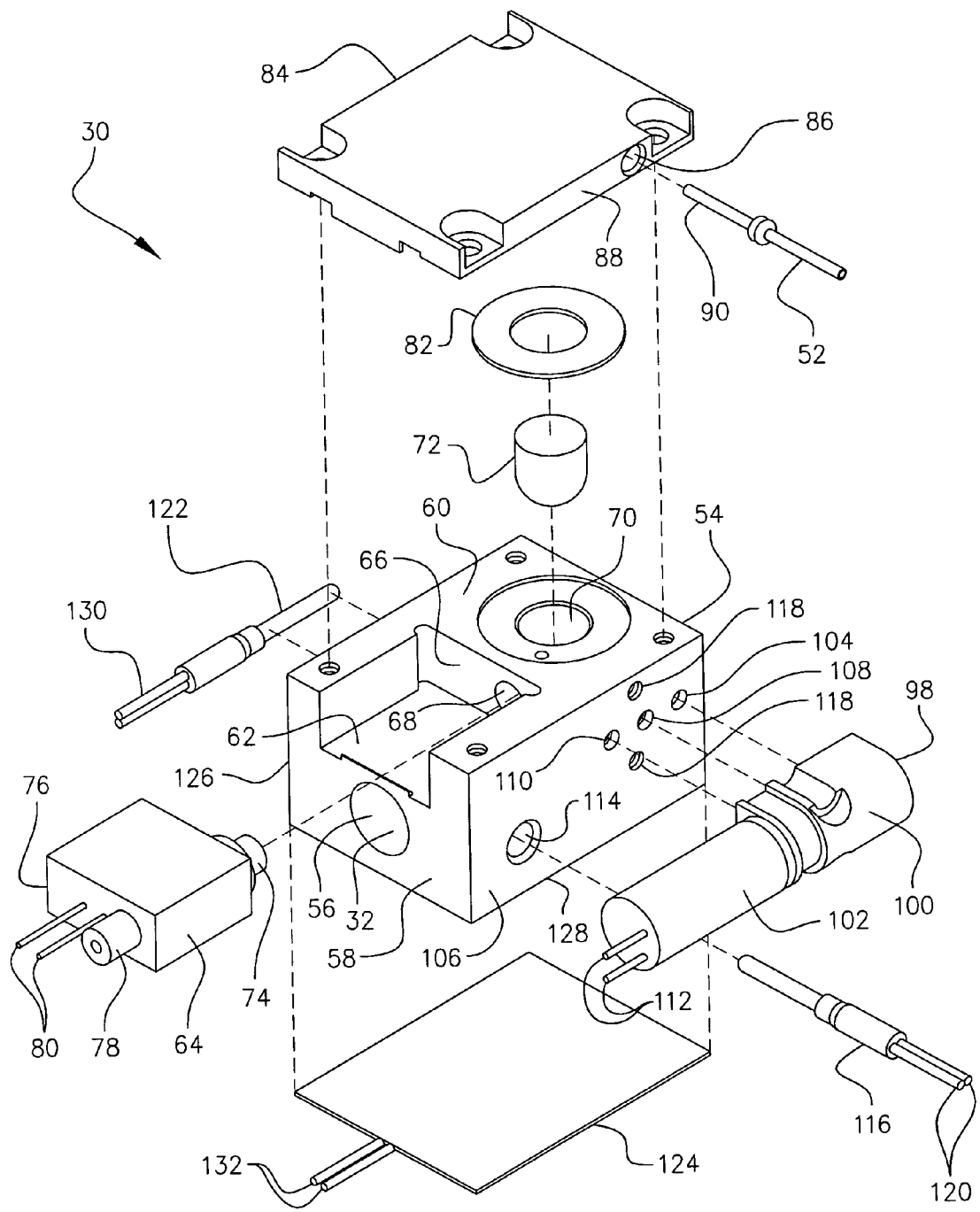
FIG. 7 is an exploded view of the breath sampling housing.
Figure 8:
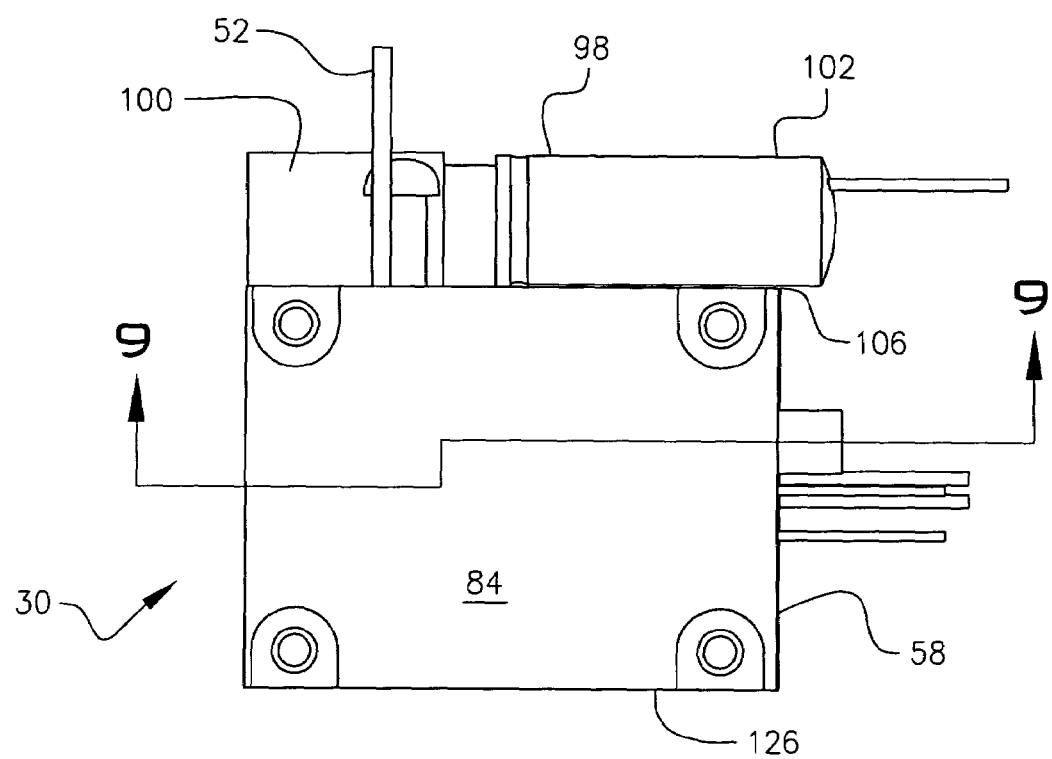
FIG. 8 is a left side elevational view of the breath sampling housing.

Referring now to FIG. 7, an exploded view of breath sampling housing 30 is shown illustrating the components used therein. Breath sampling housing 30 includes a body portion 54 having a first channel 56 (see also FIG. 9) formed there through. Body portion 54 is rectangular-shaped and includes a front end 58 and a top side 60 which has a cut-away portion 62 which seats a fuel cell 64. In the preferred embodiment, fuel cell 64 is a dry electrochemical fuel cell which operates by producing an electrical signal in response to a chemical reaction across the cell (the difference in the chemical reaction). Fuel cell 64 is employed as an alcohol specific fuel cell. A dry electrochemical fuel cell is preferred over other fuel cells, such as thermo-based cells, although nothing herein limits the use of other known fuel cells that are capable of measuring the presence of alcohol.

With continuing reference to FIG. 7, along a back wall 66 of cut-away portion 62, is a second channel 68 formed in body portion 54 which communicates with a passageway 70 and an entrance port 74 of fuel cell 64. Passageway 70 also seats a water filter 72. On an opposed side 76 of fuel cell 64 from that of fuel cell entrance port 74 is an exhaust port 78 and a pair of electrical contacts 80 which bundle together and communicate with PCB 25 through first connector 40. Of the two electrical contacts 80 of fuel cell 64, one provides power to fuel cell 64 while the other provides a pathway to send an electrical signal to PCB 25. Water filter 72 sits within passageway 70 and is held down by a gasket 82 which in turn is held down by a cover 84. Cover 84 attaches to body portion top side 60 by screws and also works to enclose and retain fuel cell 64 seated within cut-away portion 62. Cover 84 has a small aperture 86 formed along a right side wall 88 for receiving a distal end 90 of capillary tube 52. A proximal end 92 of capillary tube 52 is attached to pressure transducer 46 at an entrance port 94 thereon (see FIG. 6). Aperture 86 communicates with passageway 70 for permitting a small portion of the gas sample to reach pressure transducer 46 through capillary tube 52. Water filter 72 is constructed from a cork-like or sponge-like material and works to eliminate water from the gas sample while permitting alcohol vapors to pass through to fuel cell 64. The elimination or reduction of water from the gas sample ensures that fuel cell 64 is not exposed to excessive moisture which can lead to cell saturation which in turn can lead to faulty readings and cell failure.

As shown in FIG. 7, breath sampling housing also contains a solenoid valve 98 having a mounting head 100 and a valve portion 102 in air passageway communication. Solenoid valve 98 is a normally open valve. Mounting head 100 has an outwardly extending peg (not shown) on an inner surface for inserting within a peg receiving aperture 104 formed in a right side wall 106 of breath sampling housing body portion 54. Two screw bores 118 are also formed in breath sampling housing body portion right side wall 106 for receiving a pair of screws and retaining solenoid valve 98 up against body portion 54. Also formed through breath sampling housing body portion right side wall 106, are an entrance channel 108 and an exhaust channel 110 for solenoid valve 98 which axially align with reciprocal entrance and exhaust ports (not shown) formed through the inner surface of solenoid valve mounting head 100 which then communicates with valve portion 102. Entrance channel 108 leads from passageway 70 behind water filter 72, while exhaust channel 110 leads to fuel cell entrance port 74 (see FIG. 9). Solenoid valve 98 also contains a pair of electrical contacts 112, a first for providing power to solenoid valve 98 and a second for receiving an electrical signal which forces the valve to remain open and then to close for a finite time as instructed by a microprocessor (to be discussed in further detail hereinafter). As stated above, solenoid valve 98 is normally open. This acts as a "fail-safe" feature in case the valve fails. It is not desirable for the interlock device of the present invention to a give a false negative reading, or a "Pass" result, if in fact the blood alcohol content of the test taker has exceeded the predetermined threshold. If the valve is closed and has failed, then the test result may be a "Pass" when in fact the test taker is actually intoxicated, or has at least exceeded the threshold setting for the particular interlock device, due to the fact that fuel cell 64 would not see any alcohol vapors pass across the cell. A false negative may then permit the vehicle to be operated by an intoxicated driver. In an alternate embodiment, the interlock device of the present invention includes a valve open/close position sensor to indicate if the valve is not in its correct position. In such alternate embodiment, the interlock device would be programmed such that a test could not be administered if the valve is in the wrong position. In the preferred embodiment, solenoid valve 98 is closed during the initialization process ("Warm-Up"), but then returns to a normally open state.

With continuing reference to FIG. 7, a temperature sensor bore 114 is also formed through breath sampling housing body portion right side wall 106 directly below valve portion 102 of solenoid valve 98. Temperature sensor bore 114 is in communication with breath sampling channel 32. A breath temperature sensor 116, such as a thermistor, is inserted within bore 114 and is used to measure the temperature of the gas sample entering breath sampling channel 32 (see FIG. 5), thereby ensuring that the gas sample is an actual human breath from that moment in time and not some other gas used in an attempt to circumvent the interlock device. Breath temperature sensor 116 also has a pair of electrical contacts 120 for providing power to sensor 116 and for providing a pathway for a signal generated in response to a temperature measurement made by sensor 116. The two electrical contacts 120 are bundled together and couple to PCB 25 at first connector 40.

With further reference to FIG. 7, breath sampling housing 30 also includes a housing temperature sensor 122 and a housing heater 124. Housing temperature sensor 122 mounts along a left side wall 126 of body portion 54 while housing heater 124 mounts along a bottom side 128 of body portion. In the preferred embodiment, housing temperature sensor 122 is also a thermistor and housing heater 124 is a strip of heating tape. A strip of tape (not shown) can be wrapped around body portion top and bottom sides, 60 and 128, and left side wall 126 to enclose and retain housing temperature sensor 122 and housing heater 124. Housing temperature sensor 122 also has a pair of electrical contacts 130 for providing power thereto and a pathway for an electrical signal in response to a temperature measurement made by temperature housing sensor 122. Housing heater 124 has a pair of electrical leads 132 for providing power thereto. Both the pair of contacts and the pair of leads, 130 and 132 respectively, are bundled together and connect to PCB 25 at first connector 40. Housing temperature sensor 122 is used to monitor the current temperature of breath sampling housing 30 while housing heater 124 is used to warm up breath sampling housing 30 and to hold the temperature of housing 30 slightly above human body temperature and thereby avoid the development of condensation.

Referring to FIG. 15, the manner in which a gas sample enters breath sampling housing 30 and is subsequently measured is illustrated. As shown, the interlock device of the present invention includes a microprocessor 134 (mounted on PCB 25 within handset 10). Microprocessor 134 is coupled to LED display screen 12. Those components enclosed within breath sampling housing 30 are shown to be within the dotted lines represented on FIG. 15, while those components attached to the outer walls of breath sampling housing are shown to be positioned juxtaposed the same dotted lines. As shown, a gas sample from a human breath enters breath sampling channel 32 of breath sampling housing 30 from breath intake channel entrance port 34. A portion of the gas sample enters passageway 70 and is filtered by water filter 72. A portion of that gas sample is directed away from passageway 70 through aperture 86, into capillary 52 and into pressure transducer 46 through pressure transducer entrance port 94 whereby a pressure reading is measured. The remaining water filtered gas sample is expelled from passageway 70 through entrance channel 108 and into solenoid valve 98. If the valve is open, the gas sample is permitted to pass through exhaust channel 110 and into fuel cell 64 at fuel cell entrance port 74. Any remaining un-needed gas sample is then expelled through fuel cell exhaust port 78.

With continuing reference to FIG. 15, it is shown that solenoid valve 98, fuel cell 64 and pressure transducer 46 are all in communication with microprocessor 134. Microprocessor 134 first initiates a warm-up procedure before any test is taken to stabilize handset 10. Not until LED display screen 12 says "Blow Now" (or some other like instruction), can a test be taken. At such time, a person blows into mouthpiece 26 (see FIG. 3). Microprocessor instructs solenoid valve 98 to remain open for a finite period of time, for example, between 100 and 700 mS in response to detecting a minimal pressure measurement. This range allows for the accommodation of variable conditions. Fuel cell 64 measures the alcohol content of that gas sample and sends this measured reading to microprocessor 134. Some finite amount of time after solenoid valve 98 opens, microprocessor 134 takes a series of pressure measurements from pressure transducer 46. An algorithm embedded upon microprocessor 134 then calculates an offset value to apply to the measured value taken by fuel cell 64 to calculate a more accurate reading of the blood alcohol content of the gas sample. The results of this process are then used to determine whether the vehicle's ignition system can be engaged if the vehicle is powered off. A "Pass" or "Fail" message appears on LED screen display 12 depending on the results of the test. If the vehicle's power system is already running, then the results of the test will be displayed on LED display screen 12, but the power to the vehicle will not he disengaged. However, the novel interlock device of the present invention can sound the horn and flash the lights, if so desired, to draw attention to the rolling repeat test violator.

A dated data log is stored on microprocessor 134 in handset 10 and is used for recording a plurality of different events, including, but not limited to, when the interlock device was powered on and powered off, if any attempts at circumvention was attempted, results of all tests, if the vehicle's engine was idling for any amount of time, and if required tests where not performed when instructed by the interlock device (i.e., rolling repeat tests). The information in the data log can be downloaded to a PC, a laptop, personal digital assistant (PDA) or any other kind of like computing and digital storage device by interfacing with handset 10 through a data port 136 located along a side portion of handset 10 (see FIGS. 3, 4 and 6). In the preferred embodiment, data port 136 is a mini USB B port. However, any type of known data port can be employed. Further, a wireless transceiver can be employed to download data from the data log using any known wireless transmitting technology. In addition to downloads, uploads can also be effected through data port 136 for calibrating the interlock device, for performing maintenance, for setting preferences and for updating the software embedded on microprocessor 134.

Figure 13:
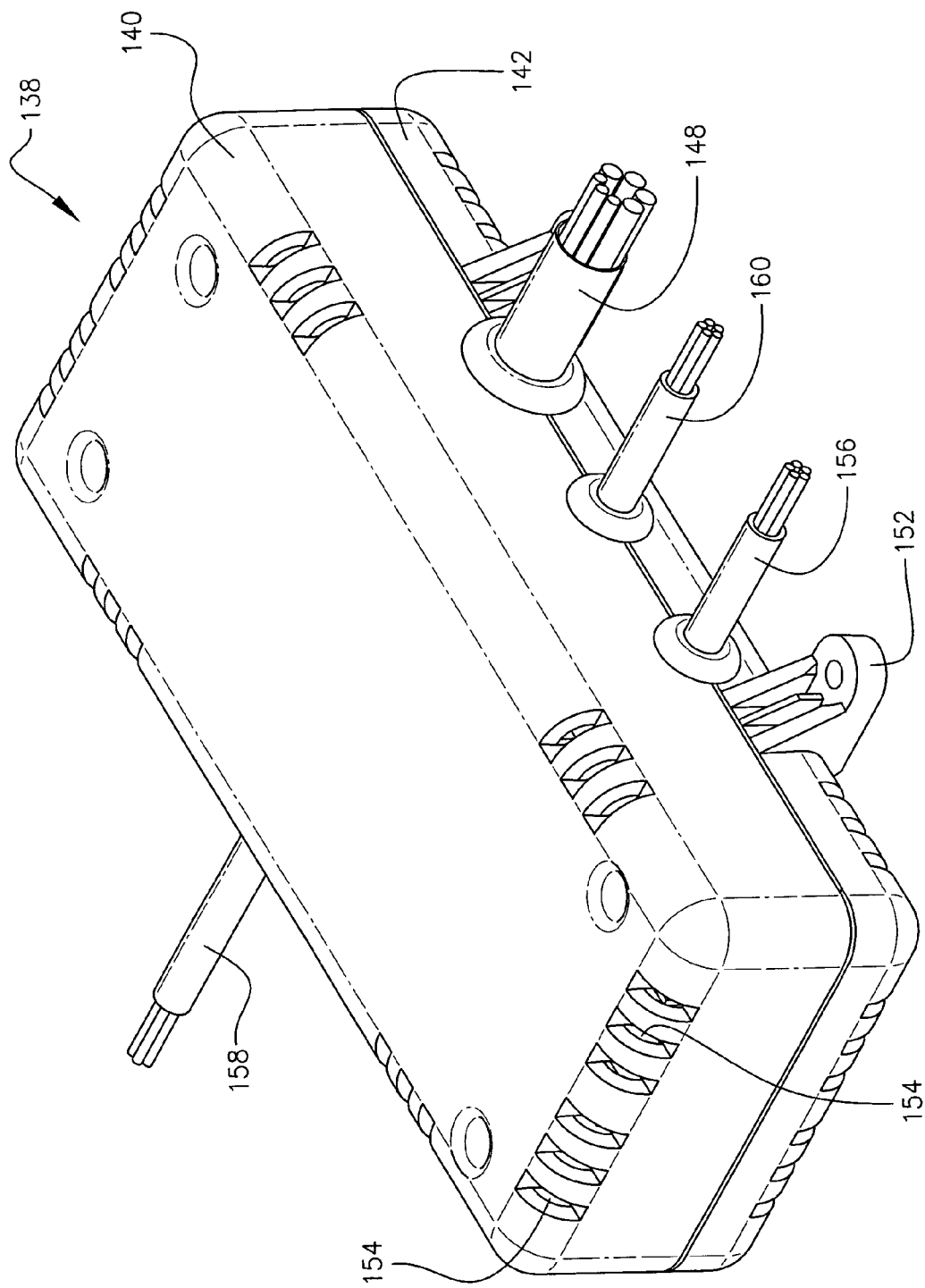
FIG. 13 is a perspective view of a base unit employed with the interlock device of the present invention.
Figure 14:
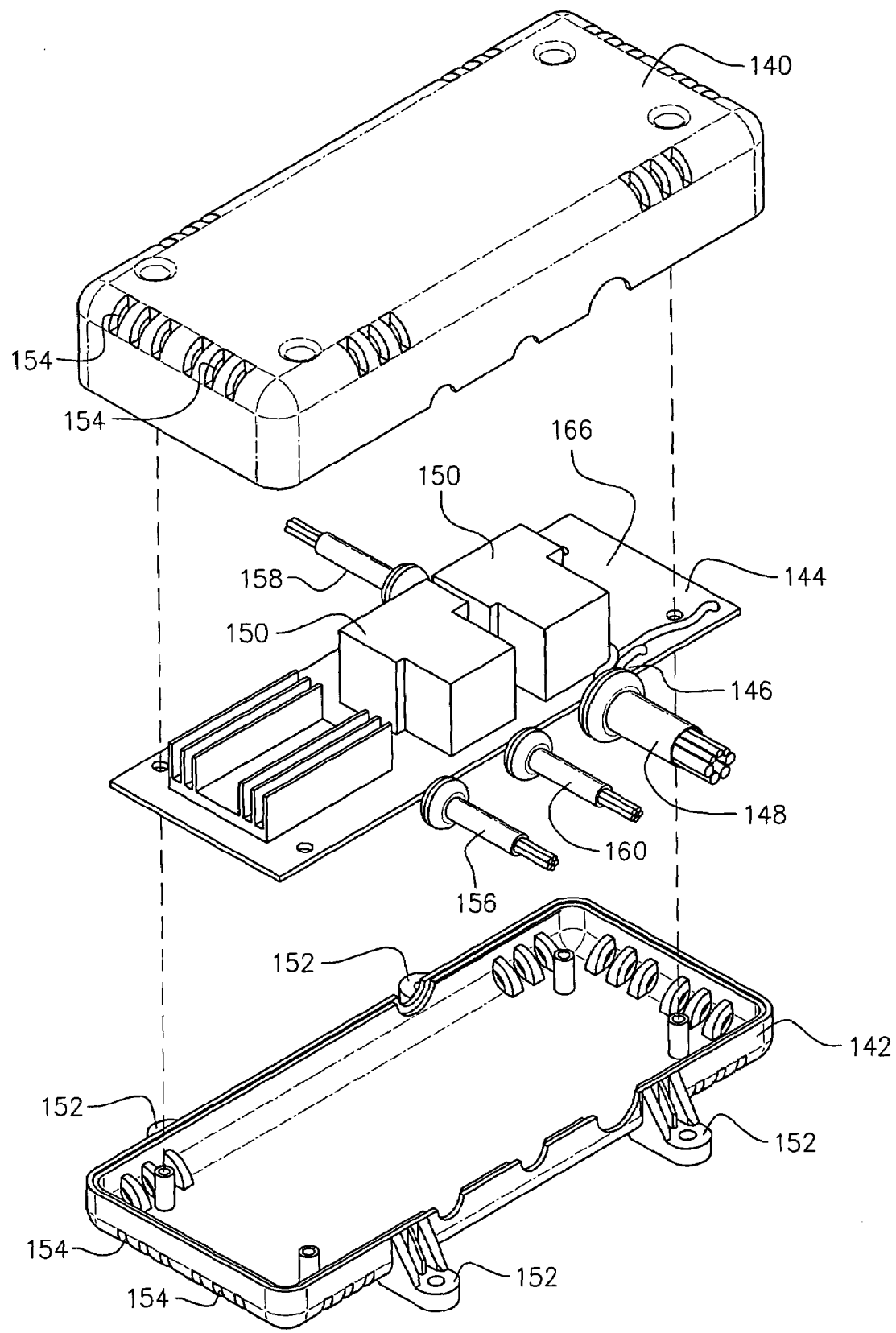
FIG. 14 is an exploded view of the base unit employed with the interlock device of the present invention.

As shown in FIG. 13, the interlock device of the present invention also includes a base unit 138. As shown in FIG. 14, base unit 138 includes a top and bottom housing member, 140 and 142 respectively, enclosing a printed circuit board (PCB) 144. Base unit 138 is coupled to handset 10 by a detachable cable 148 which terminates on PCB 144 at connector 146. In the preferred embodiment, PCB 144 has a pair of relays 150 mounted upon a top side 166 of PCB 144. The pair of relays 150 are connected in series with a starter mechanism (not shown) and the light and horn switching system of a vehicle. Relays 150 react in accordance with instructions received from microprocessor 134 which processes the gas sample test (sobriety test). Relays 150 permit the starting mechanism of a vehicle to operate if a person has passed the sobriety test and preclude the starting mechanism if the person has failed the sobriety test. Relays 150 are also used to sound the horn and flash the lights of the vehicle in response to a failed test during rolling operation of the vehicle. Additional relays could be employed within base unit 138 to operate or preclude operation of other features of a vehicle in response to a pass or failed test or to signal law enforcement or a supervising agency in response to a failed test.

Although the threshold of the sobriety test is adjustable, it is set by the manufacturer or supervising agency and can not be adjusted by the user of the interlock device. The sobriety threshold setting is effected by interfacing with a computing device through data port 136. In the preferred embodiment, the sobriety threshold is set at 0.03%. Base unit 138 can be mounted within the vehicle in a non-obtrusive location by a plurality of screws inserted through mounting wings 152. Top and bottom housing members, 140 and 142 respectively, of base unit 144 include a plurality of heat dissipation vents 154 formed throughout the outer peripheral of housing members 140 and 142.

With continuing reference to FIG. 14, it is shown that PCB 144 is provided power by cable 156 connected to a power source (not shown) of the vehicle in which the interlock device is mounted. A pair of auxiliary connectors, AUX 1 and AUX 2, 158 and 160 respectively, are coupled to PCB 144 for other interfacing uses, such as, for example, personal identification and position location features. In the preferred embodiment, AUX 1 and AUX 2 are RS-232 ports, although other data interfacing ports can be employed. Examples of personal identification features include, but are not limited to, retina scans, voice recognition, fingerprint verification and dental imprints. Examples of position location features include cellular and satellite phone interface, GPS (Global Positioning System), LORAN and unique beacon indicators.

Figure 16:
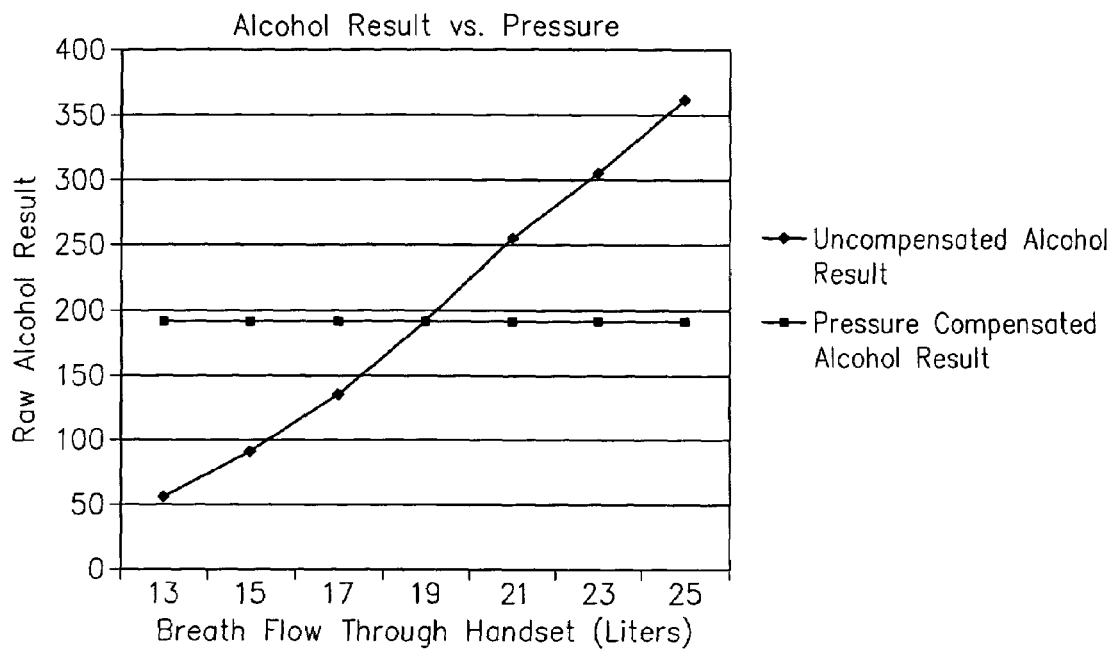
FIG. 16 is a first graph illustrating a raw alcohol measurement (test result) versus breath flow (pressure) through the handset.
Figure 17:
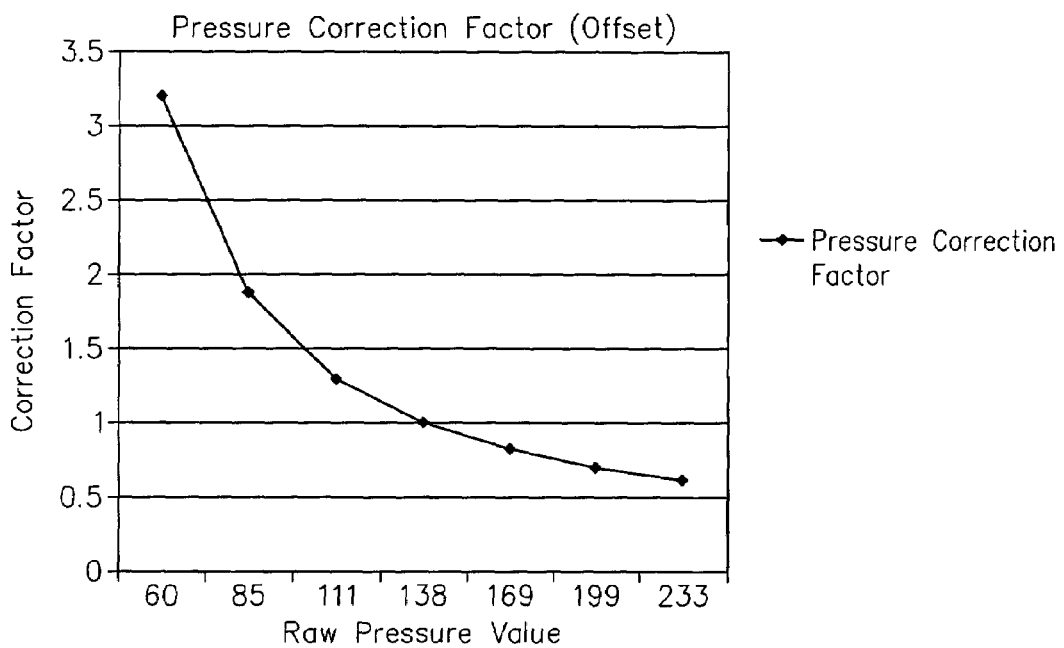
FIG. 17 is a second graph illustrating a pressure correction factor curve (offset) correlating to a raw pressure value.

Referring to FIGS. 16 and 17, it is shown how algorithmic pressure compensation is used in the interlock device of the present invention to provide an accurate measurement of the blood alcohol content of a person utilizing the device. As stated before, pressure transducer 46 does not control the opening and closing of solenoid valve 98 as seen in the prior art inventions. In the prior art, pressure transducers have been used to provide a constant volume of air to a fuel cell based upon fluctuating pressure by controlling the opening and closing of a valve upstream from a fuel cell. In the present invention, pressure transducer 46 and solenoid valve 98 operate independently from one another to provide a variable flow to fuel cell 64 based upon a threshold pressure being exceeded or not being met. An algorithmic offset is calculated in microprocessor 134 to provide a pressure compensated alcohol result that is constant, without regard to pressure, as shown in FIG. 16 as a flat line. As shown in FIG. 17, a correction factor, or offset, calculated by microprocessor 134 through the algorithm, is used to adjust the test result due to varying breath flow through handset 10. Pressure transducer 46 does not effect how long solenoid valve 98 stays open or how much breath flow is permitted to pass through to fuel cell 64. Pressure transducer 46 instead makes a measurement of the current breath flow, or pressure, and feeds that measurement to microprocessor 134 to calculate the offset. This prohibits someone from trying to fool the interlock device by introducing a low pressurized breath flow. Further, this novel approach to sampling the breath ensures that a high pressured breath flow does not saturate the fuel cell and give a false positive result.

In an alternate embodiment, the novel interlock device of the present invention can be removed from a vehicle and brought within the confines of a residence or commercial establishment. Accordingly, the novel interlock device of the present invention could be used as a home monitoring device. In such alternate embodiment, handset 10 couples to an alternate power source within the residence or commercial establishment through a power coupler. Base unit 138 can remain in the vehicle since the output relays will not be used to control a vehicle starter or ignition system. However, signaling devices within the home may be controlled and would therefore warrant removal of base unit 138 from the vehicle to be wired to said signaling devices. Handset 10 can easily interface with a home computer through data port 136 to download data logs and upload preferences and settings and software updates and to conduct scheduled calibration and/or maintenance. An example of how this alternate device would work in a home monitoring environment is as follows: the offender stands in front of a web cam while the interlock device is connected to a home computer; software installed on the home computer takes a digital picture or movie of the offender taking the test; the time is stamped on the picture or movie along with the results of the test; the test results are then transmitted to a host computer (supervising agency) over the Internet, by a proprietary hard-wired connection or by wireless transmission. The software can additionally be programmed to immediately notify a predetermined monitoring service or agency in the event of a failed or refused test.

Equivalent elements can be substituted for the ones set forth above such that they perform in the same manner in the same way for achieving the same result.

What is claimed is:

1. A sobriety interlock device having an output coupled to a starter mechanism of a motorized vehicle for detecting the presence of alcohol in a breath sample introduced into the device and for controlling the device output in response to a predetermined threshold level being exceeded, the sobriety interlock device comprising:
    a) a handset having a gas intake channel for receiving the breath sample,
    b) a breath sampling housing enclosed within the handset and having a gas sampling channel in axial alignment with the handset gas intake channel,
    c) a fuel cell positioned along the gas sampling channel of the breath sampling housing for measuring an alcohol vapor value of the breath sample,
    d) a pressure transducer located within the handset in fluid communication with the gas sampling channel of the breath sampling housing for measuring a pressure value of the breath sample,
    e) a microprocessor located within the handset in electrical communication with the fuel cell and the pressure transducer, the microprocessor containing an executable algorithm for determining a measured blood alcohol content of the breath sample through an offset adjustment of the measured alcohol vapor value in relation to the measured breath sample pressure value, the microprocessor applying a signal to the output of the interlock device dependent on the results of the measured blood alcohol content as compared to the predetermined threshold level;
    f) a solenoid valve positioned upstream from the fuel cell along the gas sampling channel of the breath sampling housing for limiting the size of the breath sample across the fuel cell by opening for a finite period of time, the solenoid valve having a normally open state; and
    g) a power source coupled to the handset.

2. The sobriety interlock device of claim 1, wherein the solenoid valve is electrically coupled to the microprocessor and opens for a predetermined period of time in response to the microprocessor receiving a signal.

3. The sobriety interlock device of claim 2, wherein the predetermined period of time that the solenoid valve opens is in the range of 100 to 700 mS, the microprocessor sending a control signal to open and close the solenoid valve.

4. The sobriety interlock device of claim 1, further comprising the handset having a top portion and a front and back housing member, the gas intake channel of the handset disposed along the top portion thereof and having an entrance port formed through the handset front housing member and an exhaust port formed through the handset back housing member.

5. The sobriety interlock device of claim 1, further comprising a mouthpiece attached to an entrance port of the handset gas intake channel.

6. The sobriety interlock device of claim 1, further comprising a temperature sensor disposed within the gas sampling channel of the breath sampling housing for measuring the breath sample introduced into the interlock device, the temperature sensor electrically coupled to the microprocessor.

7. The sobriety interlock device of claim 1, further comprising a water filter mounted within a passageway in fluid communication with the gas sampling channel of the breath sampling housing upstream from the fuel cell, the water filter eliminating water from the breath sample while permitting alcohol vapors to pass through to the fuel cell.

8. The sobriety interlock device of claim 7, wherein the pressure value of the breath sample is measured by the pressure transducer after the breath sample has passed into the water filter.

9. The sobriety interlock device of claim 8, further comprising a capillary tube having a proximal and distal end, the capillary tube providing fluid communication between the breath sampling housing and the pressure transducer, the capillary tube proximal end inserted within an aperture formed in the breath sampling housing and the capillary tube distal end inserted within an entrance port of the pressure transducer.

10. The sobriety interlock device of claim 1, wherein the fuel cell is a dry electrochemical fuel cell.

11. The sobriety interlock device of claim 1, further comprising at least one accelerometer for measuring movement of the motorized vehicle.

12. The sobriety interlock device of claim 1, further comprising a display screen electrically coupled to the microprocessor for displaying messages relative to the operation and test results of the interlock device.

13. The sobriety interlock device of claim 1, further comprising:
   a) a housing sensor for measuring the temperature of the breath sampling housing, the housing sensor mounted juxtaposed an outer side wall of the breath sampling housing and electrically coupled to the microprocessor, and
   b) a housing heater for increasing the temperature of the breath sampling housing when the temperature of the housing falls below a predefined tolerant level temperature, the housing heater mounted along a bottom side of the breath sampling housing and electrically coupled to the microprocessor.

14. The sobriety interlock device of claim 1, further comprising a base unit electrically coupled to the handset, the base unit including the output for the interlock device and having a microprocessor for interfacing with the handset microprocessor and receiving the signal dependent on the results of the measured blood alcohol content as compared to predetermined threshold level.

15. The sobriety interlock device of claim 1, wherein the output of the interlock device comprises at least one relay.

16. The sobriety interlock device of claim 1, further comprising data interfacing means for coupling to a computing device, the data interfacing means electrically coupled to the microprocessor.

17. The sobriety interlock device of claim 16, further comprising a data log stored on a computing device readable storage medium of the handset, the data log accessible through the data interfacing means.

18. A sobriety interlock device having an output coupled to a starter mechanism of a motorized vehicle having a power source, the interlock device measuring the blood alcohol content of a vehicle operator by detecting the presence of alcohol in a breath sample introduced into the device by the operator, the interlock device output effected in response to a predetermined threshold level being exceeded, the interlock device coupled to the vehicle power source, the sobriety interlock device comprising:
   a) a handset having a gas intake channel for receiving the breath sample of the vehicle operator, the gas intake channel having an entrance port and an exhaust port formed through the handset,
   b) a breath sampling housing enclosed within the handset and having a gas sampling channel in axial alignment with the handset gas intake channel positioned intermediate the handset gas intake channel entrance and exhaust ports,
   c) a fuel cell positioned along the gas sampling channel within the breath sampling housing for measuring an alcohol vapor value of the breath sample of the vehicle operator,
   d) a pressure transducer in fluid communication with the gas sampling channel of the breath sampling housing for measuring a pressure value of the breath sample of the vehicle operator, the pressure transducer having an air entrance port,
   e) a microprocessor coupled to the fuel cell and the pressure transducer, the microprocessor containing an executable algorithm for determining the blood alcohol content of the vehicle operator from the breath sample introduced into the interlock device wherein an offset adjustment is made to the measured alcohol vapor value in response to the measured breath sample pressure value, the microprocessor applying a signal to the output of the interlock device dependent on the results of the measured blood alcohol content as compared to the predetermined threshold level;
   f) a solenoid valve positioned upstream from the fuel cell along the gas sampling channel of the breath sampling housing, the solenoid valve in a normally open state, the solenoid valve limiting the size of the breath sample across the fuel cell by remaining open f or a predetermined time, the solenoid valve coupled to the microprocessor and changing states in response to receipt of a control signal from the microprocessor, the solenoid valve changing from its normally open state to a closed state when energized; and
   g) a base unit enclosing the interlock device output coupled to the handset.

19. The sobriety interlock device of claim 18, further comprising a temperature sensor disposed within the gas sampling channel of the breath sampling housing for measuring the breath sample of the vehicle operator introduced into the interlock device, the temperature sensor coupled to the microprocessor.

20. The sobriety interlock device of claim 18, further comprising a water filter mounted within a passageway in fluid communication with the gas sampling channel of the breath sampling housing upstream from the fuel cell, the water filter eliminating water from the breath sample while permitting alcohol vapors to pass through to the fuel cell.

21. The sobriety interlock device of claim 18, further comprising a capillary tube having a proximal and distal end, the capillary tube providing fluid communication between the breath sampling housing and the pressure transducer, the capillary tube proximal end inserted within an aperture formed in the breath sampling housing, the capillary tube distal end inserted within the pressure transducer air entrance port.

22. The sobriety interlock device of claim 18, further comprising at least one accelerometer for measuring movement of the motorized vehicle.

23. The sobriety interlock device of claim 18, further comprising a display screen enclosed within the handset and coupled to the microprocessor, the display screen displaying messages relative to the operation and test results of the interlock device.

24. The sobriety interlock device of claim 18, further comprising:
   a) a temperature housing sensor for measuring a current temperature of the breath sampling housing, the temperature housing sensor mounted juxtaposed along an outer side wall of the breath sampling housing, the temperature housing sensor coupled to the microprocessor, and
   b) a housing heater for increasing the temperature of the breath sampling housing when the temperature of the housing falls below a predefined tolerant level temperature as measured by the temperature housing sensor, the housing heater mounted along a bottom side of the breath sampling housing and coupled to the microprocessor.

25. The sobriety interlock device of claim 18, further comprising:
   a) data interfacing means for coupling to a computing device, the data interfacing means coupled to the microprocessor, and
   b) a data log stored on a computing device readable storage medium of the handset, the data log accessible through the data interfacing means.

26. The sobriety interlock device of claim 18, wherein the microprocessor is enclosed within the handset along a printed circuit board and communicates with the base unit by a high speed serial data interface.

27. The sobriety interlock device of claim 18, further comprising the breath sampling housing having a cut-away portion formed along a front side thereof, the cut-away portion seating and retaining the fuel cell within the breath sampling housing.

28. A vehicle sobriety interlock device for measuring the blood alcohol content of a vehicle operator by detecting the presence of alcohol in a breath sample introduced into the device by the operator, the interlock device mounted within close proximity of a driver's seat of a vehicle, the interlock device comprising:
   a) a handset having a gas intake channel for receiving the breath sample of the vehicle operator, the gas intake channel having an entrance port and an exhaust port formed through the handset,
   b) a breath sampling housing enclosed within the handset and having a gas sampling channel in axial alignment with the handset gas intake channel positioned intermediate the handset gas intake channel entrance and exhaust ports,
   c) an electrochemical fuel cell positioned along the gas sampling channel within the breath sampling housing for measuring an alcohol vapor value of the breath sample of the vehicle operator,
   d) a pressure transducer connected along the gas sampling channel of the breath sampling housing by a capillary tube, the pressure transducer measuring a pressure value of the breath sample of the vehicle operator,
   e) a solenoid valve positioned upstream from the fuel cell in fluid communication with the gas sampling channel of the breath sampling housing, the solenoid valve limiting the size of the breath sample across the fuel cell by remaining open for a predetermined amount of time, the solenoid valve held in a normally open state,
   f) a microprocessor coupled to the fuel cell, the pressure transducer and solenoid valve, the microprocessor containing an executable algorithm for determining the blood alcohol content of the vehicle operator from the breath sample introduced into the interlock device wherein an offset adjustment is made to the measured alcohol vapor value in response to the measured breath sample pressure value, the microprocessor enclosed within the handset,
   g) a base unit enclosing an output of the interlock device, the base unit communicating with the microprocessor within the handset, the output precluding a starter mechanism of the vehicle from engaging if a signal received from the handset microprocessor has determined that the blood alcohol content of the breath sample of the vehicle operator exceeds a predetermined threshold level; and
   h) a power source coupled to the handset and the base unit.

29. The sobriety interlock device of claim 28, further comprising a breath temperature sensor mounted within the gas sampling channel through a bore formed in the breath sampling housing, the breath temperature sensor measuring the breath sample of the vehicle operator introduced into the interlock device, the temperature sensor coupled to the microprocessor within the handset.

30. The sobriety interlock device of claim 28, further comprising a water filter mounted within a passageway in fluid communication with the gas sampling channel of the breath sampling housing upstream from the fuel cell and the solenoid valve such that the solenoid valve is positioned intermediate the water filter and the fuel cell, the water filter eliminating water from the breath sample while permitting alcohol vapors to pass thereby.

31. The sobriety interlock device of claim 28, further comprising at a pair of accelerometers for measuring movement of the motorized vehicle along an X and Y axis, respectively.

32. The sobriety interlock device of claim 28, further comprising a display screen mounted upon the handset and coupled to the microprocessor, the display screen displaying messages relative to the operation and test results of the interlock device.

33. The sobriety interlock device of claim 28, further comprising:
   a) the breath sampling housing including a body portion in which the gas sampling channel is formed, the body portion having first and second opposed outer side walls,
   b) the solenoid valve mounted along the first outer side wall of the body portion,
   c) an air entrance channel and an air exhaust channel formed through the body portion first outer side wall in fluid communication with solenoid valve,
   d) the air entrance channel positioned between the water filter and the solenoid valve,
   e) the air exhaust channel positioned between the solenoid valve and an entrance port of the fuel cell, and
   f) the fuel cell including an exhaust port for expelling any unused breath sample introduced into the handset.

34. The sobriety interlock device of claim 28, further comprising:
   a) a temperature housing sensor for measuring a current temperature of the breath sampling housing, the temperature housing sensor mounted juxtaposed along an outer side wall of the breath sampling housing, the temperature housing sensor coupled to the microprocessor within the handset, and b) a housing heater for increasing the temperature of the breath sampling housing when the temperature of the housing falls below a predefined tolerant level temperature as measured by the temperature housing sensor, the housing heater mounted along a bottom side of the breath sampling housing and coupled to the microprocessor.

35. The sobriety interlock device of claim 28, further comprising:
   a) data interfacing means for coupling to a computing device, the data interfacing means coupled to the microprocessor within the handset, and
   b) a data log stored on a computing device readable storage medium of the handset, the data log accessible through the data interfacing means.

36. The sobriety interlock device of claim 28, further comprising at least one auxiliary port disposed within the handset and coupled to the microprocessor.

37. The sobriety interlock device of claim 28, further comprising a speaker coupled to the microprocessor for providing audio signaling relative to operation of the interlock device.

38. A sobriety interlock device coupled to a starter mechanism of a vehicle and having an output coupled to a computing device, the sobriety interlock device detecting the presence of alcohol in a breath sample introduced into the device and for controlling the device output in response to a predetermined threshold level being exceeded, the sobriety interlock device comprising:
   a) a handset having a gas intake channel for receiving the breath sample,
   b) a breath sampling housing enclosed within the handset and having a gas sampling channel in axial alignment with the handset gas intake channel,
   c) a fuel cell positioned along the gas sampling channel of the breath sampling housing for measuring an alcohol vapor value of the breath sample,
   d) a pressure transducer located within the handset in fluid communication with the gas sampling channel of the breath sampling housing for measuring a pressure value of the breath sample,
   e) a microprocessor located within the handset in electrical communication with the fuel cell and the pressure transducer, the microprocessor containing an executable algorithm for determining a measured blood alcohol content of the breath sample through an offset adjustment of the measured alcohol vapor value in relation to the measured breath sample pressure value, the microprocessor applying a signal to the output of the interlock device dependent on the results of the measured blood alcohol content as compared to the predetermined threshold level;
   f) a solenoid valve held in a normally open state, and
   g) a power source coupled to the handset.

* * * * *